(12) United States Patent
Koop et al.

(10) Patent No.: US 10,806,932 B2
(45) Date of Patent: Oct. 20, 2020

(54) IMPLANTABLE MEDICAL DEVICE

(71) Applicant: CARDIAC PACEMAKERS, INC., St. Paul, MN (US)

(72) Inventors: Brendan Early Koop, Ham Lake, MN (US); Pramodsingh Hirasingh Thakur, Woodbury, MN (US); Qi An, Blaine, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 283 days.

(21) Appl. No.: 15/925,297

(22) Filed: Mar. 19, 2018

(65) Prior Publication Data

US 2018/0264270 A1  Sep. 20, 2018

Related U.S. Application Data

(60) Provisional application No. 62/473,882, filed on Mar. 20, 2017.

(51) Int. Cl.
| *A61N 1/365* | (2006.01) |
| *A61N 1/05* | (2006.01) |
| *A61N 1/39* | (2006.01) |
| *A61N 1/375* | (2006.01) |
| *A61N 1/372* | (2006.01) |
| *A61N 1/37* | (2006.01) |
| *A61N 1/362* | (2006.01) |

(52) U.S. Cl.
CPC .......... *A61N 1/36507* (2013.01); *A61N 1/05* (2013.01); *A61N 1/056* (2013.01); *A61N 1/0563* (2013.01); *A61N 1/362* (2013.01); *A61N 1/3702* (2013.01); *A61N 1/3756* (2013.01); *A61N 1/37211* (2013.01); *A61N 1/37229* (2013.01); *A61N 1/39* (2013.01); *A61N 1/3956* (2013.01); *A61N 1/3962* (2013.01); *A61N 1/3987* (2013.01)

(58) Field of Classification Search
CPC .......... A61N 1/056; A61N 1/365–3718; A61B 5/0402–0472
See application file for complete search history.

(56) References Cited

U.S. PATENT DOCUMENTS

| 5,331,966 A | 7/1994 | Bennett et al. |
| 6,647,292 B1 | 11/2003 | Bardy et al. |

(Continued)

FOREIGN PATENT DOCUMENTS

| WO | 2015164168 A1 | 10/2015 |
| WO | 2016148928 A1 | 9/2016 |

(Continued)

OTHER PUBLICATIONS

Moeinipour et al., "A Rare Central Venous Catheter Malposition: A Case Report," Anesth Pain Med., 4(1): 1-3, Feb. 5, 2014.

(Continued)

*Primary Examiner* — Michael W Kahelin
(74) *Attorney, Agent, or Firm* — Seager, Tufte & Wickhem LLP

(57) ABSTRACT

IMD devices and treatment methods are discussed and disclosed. An IMD having a lead adapted for placement in an internal thoracic vein (ITV) of a patient may be employed to facilitate atrial sensing. Devices may be used to communicate with one another, such communication configured to allow pacing therapy to a heart of a patient.

12 Claims, 14 Drawing Sheets

(56) References Cited

U.S. PATENT DOCUMENTS

| | | |
|---|---|---|
| 6,721,597 B1 | 4/2004 | Bardy et al. |
| 7,149,575 B2 | 12/2006 | Ostroff et al. |
| 7,655,014 B2 | 2/2010 | Ko et al. |
| 7,783,340 B2 | 8/2010 | Sanghera et al. |
| 7,818,068 B2 | 10/2010 | Meadows et al. |
| 7,962,222 B2 | 6/2011 | He et al. |
| 8,005,543 B2 | 8/2011 | Libbus et al. |
| 8,157,813 B2 | 4/2012 | Ko et al. |
| 8,386,048 B2 | 2/2013 | McClure et al. |
| 8,483,843 B2 | 7/2013 | Sanghera et al. |
| 8,543,216 B2 | 9/2013 | Carbunaru et al. |
| 8,744,572 B1 | 6/2014 | Greenhut et al. |
| 2005/0043765 A1 | 2/2005 | Williams et al. |
| 2012/0029335 A1 | 2/2012 | Sudam et al. |
| 2014/0330326 A1 | 11/2014 | Thompson-Nauman et al. |
| 2015/0025612 A1 | 1/2015 | Haasl et al. |
| 2015/0051610 A1 | 2/2015 | Schmidt et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0224320 A1 | 8/2015 | Stahmann |
| 2015/0297902 A1 | 10/2015 | Stahmann et al. |
| 2015/0360036 A1 | 12/2015 | Kane et al. |
| 2016/0038742 A1 | 2/2016 | Stahmann et al. |
| 2016/0059007 A1 | 3/2016 | Koop |
| 2016/0059022 A1 | 3/2016 | Stahmann et al. |
| 2016/0059024 A1 | 3/2016 | Stahmann et al. |
| 2016/0059025 A1 | 3/2016 | Stahmann et al. |
| 2016/0089539 A1 | 3/2016 | Gilkerson et al. |
| 2016/0228712 A1 | 8/2016 | Koop |
| 2016/0256692 A1 | 9/2016 | Baru |
| 2017/0021159 A1 | 1/2017 | Reddy et al. |
| 2017/0312510 A1* | 11/2017 | Hareland ............. A61N 1/3712 |
| 2017/0312516 A1 | 11/2017 | Jackson et al. |
| 2017/0368360 A1 | 12/2017 | Hahn et al. |
| 2018/0008829 A1 | 1/2018 | An et al. |
| 2018/0036527 A1 | 2/2018 | Reddy et al. |
| 2018/0036547 A1 | 2/2018 | Reddy |
| 2018/0133462 A1 | 5/2018 | Reddy |
| 2018/0133463 A1 | 5/2018 | Reddy |
| 2018/0133494 A1 | 5/2018 | Reddy |
| 2018/0169384 A1 | 6/2018 | Reddy et al. |
| 2018/0169425 A1 | 6/2018 | Reddy et al. |
| 2018/0178018 A1 | 6/2018 | Reddy et al. |
| 2018/0178019 A1 | 6/2018 | Reddy et al. |
| 2018/0193060 A1 | 7/2018 | Reddy et al. |
| 2018/0214686 A1 | 8/2018 | De Kock et al. |
| 2018/0256890 A1 | 9/2018 | Fuhs et al. |
| 2018/0264270 A1 | 9/2018 | Koop et al. |
| 2018/0296824 A1 | 10/2018 | De Krock et al. |
| 2018/0325480 A1 | 11/2018 | Liu et al. |
| 2018/0344200 A1 | 11/2018 | Thakur et al. |
| 2018/0344252 A1 | 11/2018 | An et al. |

FOREIGN PATENT DOCUMENTS

| | | |
|---|---|---|
| WO | 2016149262 A1 | 9/2016 |
| WO | 2018026922 A1 | 2/2018 |

OTHER PUBLICATIONS

Schuder et al., "Experimental Ventricular Defibrillation with an Automatic and Completely Implanted System," Trans. Amer. Soc. Artif. Int. Organs, XVI: 207-212, 1970.

Schuder et al., "The Role of an Engineering Oriented Medical Research Group in Developing Improved Methods and Devices for Achieving Ventricular Defibrillation: The University of Missouri Experience," PACE, 16: 95-124, Jan. 1993.

Ghosh et al., "A Rare Malposition of the Thoracic Venous Catheter Introduced via the Left Internal Jugular Vein," Indian J. Crit. Care Med., 12(4): 201-203, Oct.-Dec. 2008.

Loukas et al., "The Clinical Anatomy of the Internal Thoracic Veins," Folia Morphol, 66(1): 25-32, 2007.

Advisory Action Before the Filing of an Appeal Brief for U.S. Appl. No. 15/667,167, dated Mar. 21, 2019.

Final Office Action for U.S. Appl. No. 15/667,167, dated Jan. 10, 2019.

Non-Final Office Action for U.S. Appl. No. 15/667,167, dated Jun. 26, 2018.

Non-Final Office Action for U.S. Appl. No. 15/667,167, dated Aug. 7, 2019.

Final Office Action for U.S. Appl. No. 15/667,221, dated Apr. 11, 2019.

Non-Final Office Action for U.S. Appl. No. 15/667,221, dated Oct. 1, 2018.

Notice of Allowance and Fees Due for U.S. Appl. No. 15/667,221, dated Jul. 11, 2019.

Amendment for U.S. Appl. No. 15/667,167, dated Sep. 17, 2018.

Amendment for U.S. Appl. No. 15/667,167, dated Oct. 9, 2019.

Amendment After Final Office Action for U.S. Appl. No. 15/667,167, dated Mar. 11, 2019.

Request for Continued Examination (RCE) for U.S. Appl. No. 15/667,167, dated Apr. 10, 2019.

Amendment for U.S. Appl. No. 15/667,221, dated Dec. 21, 2018.

Amendment After Final Office Action for U.S. Appl. No. 15/667,221, dated May 22, 2019.

International Search report and Written Opinion dated May 28, 2018 for International Application No. PCT/US2018/023138.

* cited by examiner

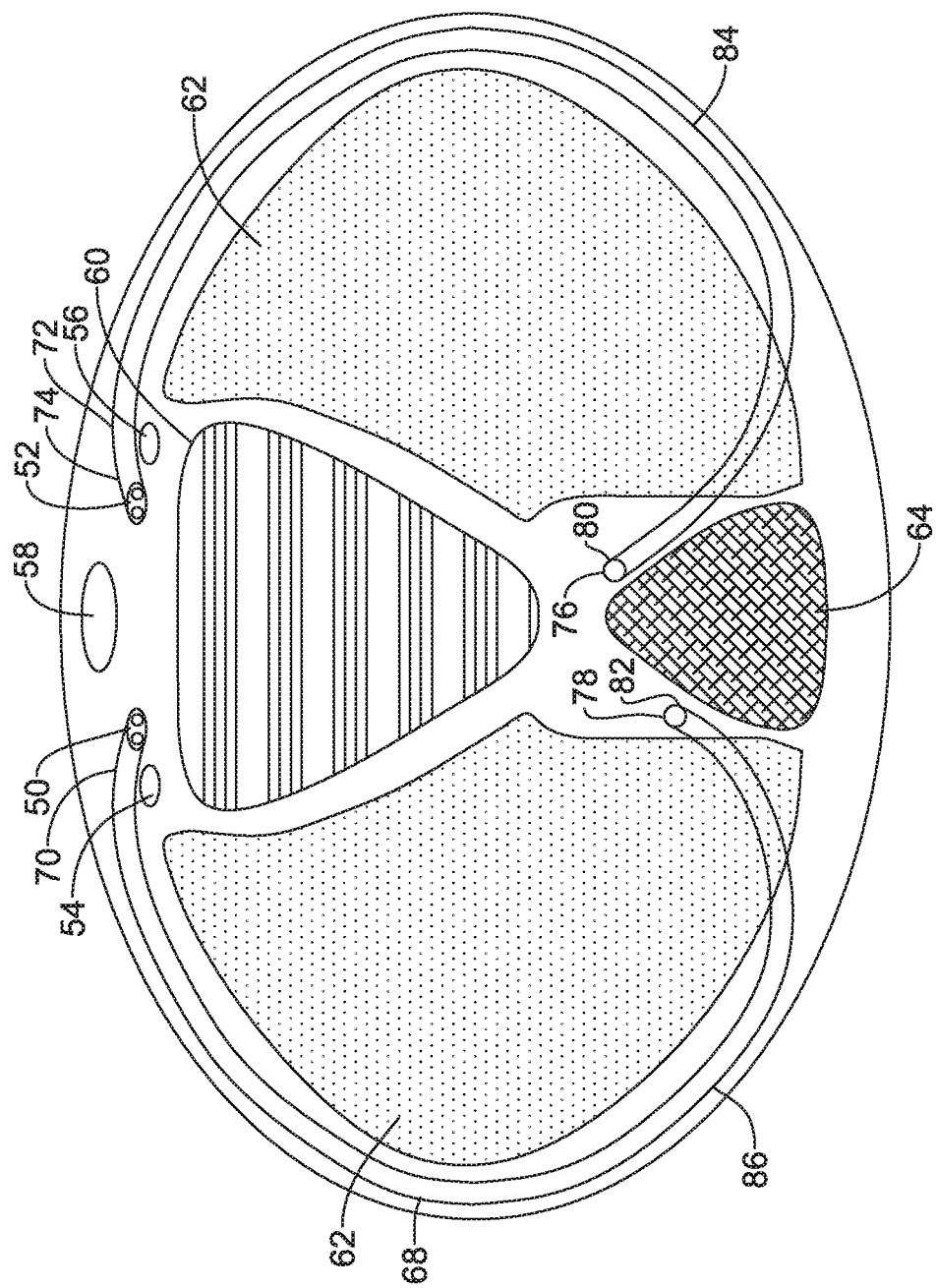

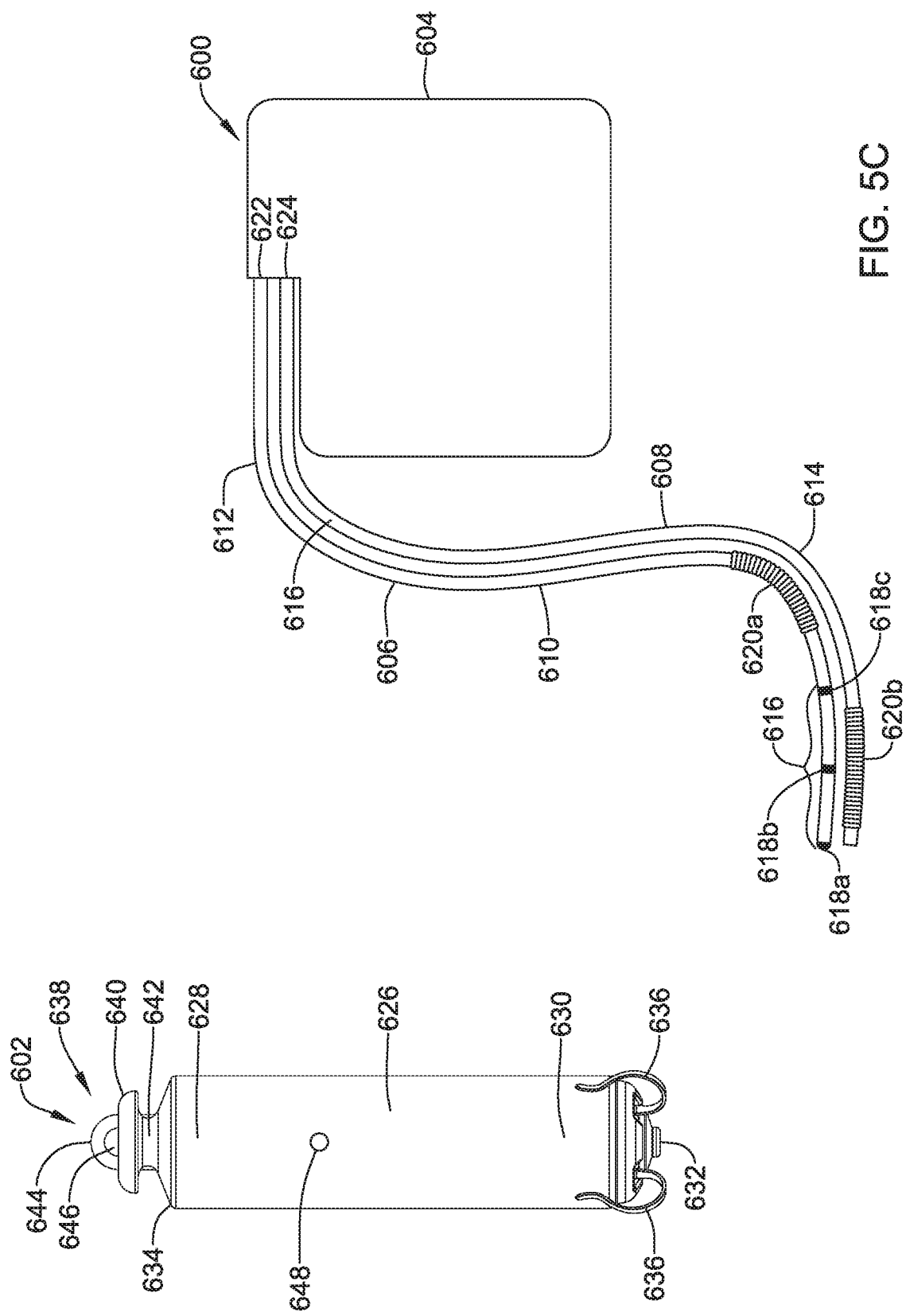

IMPLANTABLE MEDICAL DEVICE

CROSS REFERENCE TO RELATED APPLICATIONS

The present application claims the benefit of and priority to U.S. Provisional Patent Application Ser. No. 62/473,882, filed Mar. 20, 2017, titled IMPLANTABLE MEDICAL DEVICE, the disclosure of which is incorporated herein by reference.

BACKGROUND

Implantable medical devices are commonly used to perform a variety of functions, such as to monitor one or more conditions and/or delivery therapy to a patient. In some cases, an implantable medical device may simply monitor one or more conditions, such as pressure, acceleration, cardiac events, and may communicate the detected conditions or events to another device, such as another implantable medical device or an external programmer.

In some cases, an implantable medical device may be configured to deliver pacing and/or defibrillation therapy to a patient. Such implantable medical devices may treat patients suffering from various heart conditions that may result in a reduced ability of the heart to deliver sufficient amounts of blood to a patient's body. In some cases, heart conditions may lead to rapid, irregular, and/or inefficient heart contractions. To help alleviate some of these conditions, various devices (e.g., pacemakers, defibrillators, etc.) may be implanted into a patient's body. When so provided, such devices can monitor and provide therapy, such as electrical stimulation therapy, to the patient's heart to help the heart operate in a more normal, efficient and/or safe manner. In some cases, a patient may have multiple implanted devices that cooperate to monitor and/or provide therapy to the patient's heart.

What would be desirable is an implantable device that can receive cardiac signals and communicate with another implanted device within a patient. This may allow cardiac events to be recognized, analyzed, and treated more efficiently.

Overview

The present inventors have recognized, among other things, that the internal thoracic vasculature including, in particular, the internal thoracic vein (ITV), sometimes also referred to as the internal mammary vein, presents an opportunity for an additional alternative implant location. An IMD having a lead adapted for placement in the ITV of a patient may be employed to allow atrial sensing and p-waves may be analyzed from atrial signals. Devices may then be used to communicate with one another, such communication configured to allow pacing therapy to the heart of the patient.

A first non-limiting example takes the form of an implantable medical device (IMD) comprising a housing, a first lead external to the housing and adapted for placement in an ITV of a patient, the first lead including a distal portion that includes a sensing bipole adapted for atrial sensing, and a proximal portion having a proximal end that includes a connector for coupling to the housing, operational circuitry disposed within the housing and operatively coupled to the first lead, the operational circuitry including P-wave sense means configured to analyze atrial signals from the sensing bipole adapted for atrial sensing and identify a P-wave signal, and a power source disposed within the housing, operatively coupled to the operational circuitry, and configured to power the operational circuitry.

Additionally or alternatively a second non-limiting example takes the form of an IMD as in the first non-limiting example, the operational circuitry further including communication circuitry configured for communicative coupling to a second medical device, and pace command means configured to analyze the P-wave signal and cause the communication circuitry to communicate pacing therapy directions to the second medical device based on the analysis of the P-wave signal.

A third non-limiting example takes the form of a system comprising an IMD as in the second non-limiting example and a leadless cardiac pacemaker (LCP) for placement in, on or adjacent to the heart, wherein the LCP is configured as the second medical device to which the communication circuitry of the IMD, and the LCP is configured to deliver pacing therapy using the pacing therapy directions.

Additionally or alternatively a fourth non-limiting example takes the form of a system as in the third non-limiting example wherein the LCP is configured for placement in or on the right ventricle of the heart, and the pacing command means is configured to tailor the pacing therapy directions for pacing delivered from the right ventricle.

Additionally or alternatively a fifth non-limiting example takes the form of a system as in the third non-limiting example wherein the LCP is configured for placement in or on the left ventricle of the heart, and the pacing command means is configured to tailor the pacing therapy directions for pacing delivered from the left ventricle.

Additionally or alternatively a sixth non-limiting example takes the form of a system as in the third to fifth non-limiting examples wherein the pacing command means is configured to tailor the pacing therapy directions for cardiac resynchronization therapy.

Additionally or alternatively a seventh non-limiting example takes the form of a system as in the third to fifth non-limiting examples wherein the pacing command means is configured to tailor the pacing therapy directions for Vdd pacing.

Additionally or alternatively an eighth non-limiting example takes the form of an IMD or system as in the first to seventh non-limiting examples wherein the IMD is an implantable defibrillator and the first lead includes a defibrillation coil at a first location on the distal portion of the first lead, with the sensing bipole including at least two electrodes distal of the defibrillation coil on the first lead.

Additionally or alternatively a ninth non-limiting example takes the form of an IMD or system as in the first to seventh non-limiting examples wherein the IMD is an implantable defibrillator further comprising a second lead having a defibrillation coil disposed thereon, the second lead adapted for placement subcutaneously or in a substernal location.

Additionally or alternatively a tenth non-limiting example takes the form of an IMD or system as in the first to seventh non-limiting examples wherein the first lead comprises first, second and third electrodes, the first and second electrodes forming a first sensing bipole adapted for atrial sensing, and the third electrode forming, with one of the first or second electrodes, a second sensing bipole adapted for atrial sensing.

Additionally or alternatively an eleventh non-limiting example takes the form of an IMD or system as in the tenth non-limiting example wherein the operational circuitry further comprises P-wave propagation means configured to determine propagation of the P-wave signal using the first and second bipoles, observe an amplitude of the P-wave signal, and confirm detection of the P-wave signal based on the propagation and the amplitude.

Additionally or alternatively a twelfth non-limiting example takes the form of an IMD or system as in the first to eleventh non-limiting examples wherein the IMD operational circuitry further comprises communication circuitry configured for communicative coupling to a second medical device, and pace command means configured to cause the communication circuitry to communicate pacing therapy directions to the second medical device based on the analysis by the P-wave sense means.

Additionally or alternatively a thirteenth non-limiting example takes the form of an IMD or system as in the first to twelfth non-limiting examples wherein the first lead is further adapted for placement in an intercostal vein of the patient.

A fourteenth non-limiting example takes the form of an implantable system comprising a first medical device comprising a housing containing operational circuitry including sensing circuitry for sensing P-wave, the first medical device further comprising a first lead having a sensing bipole adapted for atrial sensing, the lead sized and adapted for placement in an internal thoracic vein (ITV) of a patient, a second medical device in the form of a leadless cardiac pacemaker (LCP) for placement in, on, or adjacent to the heart of the patient, wherein the first and second medical devices are configured to communicate with one another, such communication configured to allow optimization of pacing therapy delivery by the second medical device to the heart of the patient.

Additionally or alternatively a fifteenth non-limiting example takes the form of an implantable system as in the fourteenth non-limiting example wherein the first medical device is an implantable defibrillator and the first lead includes a defibrillation coil at a first location on a distal part of the lead, with the sensing bipole including at least two electrodes distal of the defibrillation coil on the lead.

Additionally or alternatively a sixteenth non-limiting example takes the form of an implantable system as in the fourteenth non-limiting example wherein the first medical device is an implantable defibrillator further comprising a second lead having a defibrillation coil disposed thereon, the second lead adapted for placement subcutaneously or in a substernal location.

Additionally or alternatively a seventeenth non-limiting example takes the form of an implantable system as in the fifteenth non-limiting example wherein the first lead comprises first, second and third electrodes, the first and second electrodes forming a first sensing bipole adapted for atrial sensing, and the third electrode forming, with one of the first or second electrodes, a second sensing bipole adapted for atrial sensing, wherein the operational circuitry is configured to determine signal propagation of the P-wave using the first and second bipoles.

Additionally or alternatively an eighteenth non-limiting example takes the form of an implantable system as in the fifteenth non-limiting example wherein the LCP is configured for placement in the right ventricle of the heart.

Additionally or alternatively a nineteenth non-limiting example takes the form of an implantable system as in the fifteenth non-limiting example wherein the LCP is configured for placement in the left ventricle of the heart.

Additionally or alternatively a twentieth non-limiting example takes the form of an implantable system as in the fifteenth non-limiting example wherein the pacing therapy comprises cardiac resynchronization therapy.

Additionally or alternatively a twenty-first non-limiting example takes the form of an implantable system as in the fifteenth non-limiting example wherein the pacing therapy comprises Vdd pacing.

Additionally or alternatively a twenty-second non-limiting example takes the form of an implantable system as in the fifteenth non-limiting example wherein the optimization of the pacing therapy delivery is achieved using the operational circuitry of the first medical device that is further configured to analyze the P-wave, determine pacing therapy delivery directions based on the analysis of the P-wave, and send the pacing therapy delivery directions to the LCP.

Additionally or alternatively a twenty-third non-limiting example takes the form of an implantable system as in the fifteenth non-limiting example wherein the lead comprises first, second and third electrodes, the first and second electrodes forming a first sensing bipole adapted for atrial sensing, and the third electrode forming, with one of the first or second electrodes, a second sensing bipole adapted for atrial sensing and the operational circuitry is further configured to determine propagation of the P-wave using the first and second bipoles, observe an amplitude of the P-wave, confirm detection of the P-wave based on the propagation and the amplitude, analyze the P-wave, determine pacing therapy delivery directions based on the analysis of the P-wave, and send the pacing therapy delivery directions to the LCP.

A twenty-fourth non-limiting example takes the form of an implantable system comprising a first medical device comprising sensing circuitry for observing an atrial cardiac signal, a lead operatively coupled to the sensing circuitry having a sensing bipole adapted for atrial sensing, the lead sized and adapted for placement in an internal thoracic vein (ITV) of a patient, first communication circuitry operatively coupled to the sensing circuitry and configured to send the atrial cardiac signal, and a housing containing the sensing circuitry and the first communication circuitry, a second medical device comprising second communication circuitry communicatively coupled to the first communication circuitry and configured to receive the atrial cardiac signal, processing circuitry configured to analyze a P-wave from the atrial cardiac signal and determine pacing therapy directions based on the analysis of the P-wave, and a housing containing the analyzing circuitry and the sensing circuitry.

Additionally or alternatively a twenty-fifth non-limiting example takes the form of an implantable system as in the twenty-fourth non-limiting example further comprising a third medical device in the form of a leadless cardiac pacemaker (LCP) for placement in, on or adjacent to the heart, comprising third communication circuitry communicatively coupled to the second communication circuitry and configured to receive the pacing therapy directions, and therapy circuitry configured to deliver the pacing therapy based on the pacing therapy directions.

Additionally or alternatively a twenty-sixth non-limiting example takes the form of an implantable system as in the twenty-fifth non-limiting example wherein the LCP is configured for placement in the right ventricle of the heart.

Additionally or alternatively a twenty-seventh non-limiting example takes the form of an implantable system as in the twenty-fifth non-limiting example wherein the LCP is configured for placement in the left ventricle of the heart.

Additionally or alternatively a twenty-eighth non-limiting example takes the form of an implantable system as in the twenty-fourth non-limiting example wherein the first medical device is an implantable pulse generator (IPG) and the sensing bipole includes at least two electrodes on a distal part of the lead.

Additionally or alternatively a twenty-ninth non-limiting example takes the form of an implantable system as in the twenty-fourth non-limiting example wherein the second medical device is an implantable defibrillator further comprising a second lead having a defibrillation coil disposed thereon, the second lead adapted for placement subcutaneously or in a substernal location.

Additionally or alternatively a thirtieth non-limiting example takes the form of an implantable system as in the twenty-fourth non-limiting example wherein the lead of the first medical device comprises first, second and third electrodes, the first and second electrodes forming a first sensing bipole adapted for atrial sensing, and the third electrode forming, with one of the first or second electrodes, a second sensing bipole adapted for atrial sensing, wherein the analyzing circuitry of the second medical device is configured to determine signal propagation of the P-wave using the first and second bipoles.

Additionally or alternatively a thirty-first non-limiting example takes the form of an implantable system as in the twenty-fourth non-limiting example wherein the pacing therapy comprises cardiac resynchronization therapy.

Additionally or alternatively a thirty-second non-limiting example takes the form of an implantable system as in the twenty-fourth non-limiting example wherein the pacing therapy comprises Vdd pacing.

Additionally or alternatively a thirty-third non-limiting example takes the form of an implantable system as in the twenty-fourth non-limiting example wherein the lead of the first medical device comprises first, second and third electrodes, the first and second electrodes forming a first sensing bipole adapted for atrial sensing, and the third electrode forming, with one of the first or second electrodes, a second sensing bipole adapted for atrial sensing and the analyzing circuitry is further configured to determine propagation of the P-wave using the first and second bipoles, observe an amplitude of the P-wave, and confirm detection of the P-wave based on the propagation and the amplitude.

A thirty-fourth non-limiting example takes the form of a method of treating a patient comprising sensing an atrial cardiac signal using a first electrode located in an internal thoracic vein (ITV) of the patient and a second electrode, the first electrode and the second electrode operatively coupled to a first medical device, analyzing a P-wave from the atrial cardiac signal using the first medical device, determining a therapy using the first medical device based on the analyzed P-wave, and sending a therapy instruction to a second medical device communicatively coupled to the first medical device.

Additionally or alternatively a thirty-fifth non-limiting example takes the form of a method as in the thirty-fourth non-limiting example further comprising delivering the therapy to the patient using the second medical device based on the therapy instruction.

Additionally or alternatively a thirty-sixth non-limiting example takes the form of a method as in the thirty-fourth non-limiting example wherein the first medical device is an implantable cardioverter defibrillator.

Additionally or alternatively a thirty-seventh non-limiting example takes the form of a method as in the thirty-fourth non-limiting example wherein the second medical device is a leadless cardiac pacemaker (LCP) located in a heart of the patient.

Additionally or alternatively a thirty-eighth non-limiting example takes the form of a method as in the thirty-fourth non-limiting example wherein the therapy comprises cardiac resynchronization therapy.

Additionally or alternatively a thirty-ninth non-limiting example takes the form of a method as in the thirty-fourth non-limiting example wherein the therapy comprises Vdd pacing.

Additionally or alternatively a fortieth non-limiting example takes the form of a method as in the thirty-fourth non-limiting example wherein the first medical device is further operatively coupled to a third electrode and the first and second electrodes form a first sensing bipole adapted for atrial sensing, and the third electrode forms, with one of the first or second electrodes, a second sensing bipole adapted for atrial sensing.

Additionally or alternatively a forty-first non-limiting example takes the form of a method as in the fortieth non-limiting example further comprising determining propagation of the P-wave using the first and second bipoles, observing an amplitude of the P-wave using the first medical device, and confirming detection of the P-wave based on the propagation and the amplitude using the first medical device.

A forty-second non-limiting example takes the form of a method of treating a patient comprising sensing an atrial cardiac signal using a first electrode structure located in an internal thoracic vein (ITV) of the patient and a second electrode structure, the first electrode structure and the second electrode structure operatively coupled to a first medical device, sending the atrial cardiac signal to a second medical device that is communicatively coupled to the first medical device, analyzing a P-wave from the atrial cardiac signal using the second medical device, determining a therapy using the second medical device based on the analyzed P-wave cardiac signal, and sending a therapy signal to a third medical device that is communicatively coupled to the second medical device.

Additionally or alternatively a forty-third non-limiting example takes the form of a method as in the forty-second non-limiting example further comprising delivering the therapy to the patient using the third medical device based on the therapy signal.

Additionally or alternatively a forty-fourth non-limiting example takes the form of a method as in the forty-second non-limiting example wherein the second medical device is an implantable cardioverter defibrillator.

Additionally or alternatively a forty-fifth non-limiting example takes the form of a method as in the forty-second non-limiting example wherein the third medical device comprises a leadless cardiac pacemaker located in a heart of the patient.

Additionally or alternatively a forty-sixth non-limiting example takes the form of a method as in the forty-second non-limiting example wherein the therapy comprises cardiac resynchronization therapy.

Additionally or alternatively a forty-seventh non-limiting example takes the form of a method as in the forty-second non-limiting example wherein the therapy comprises Vdd pacing Additionally or alternatively a forty-eighth non-limiting example takes the form of a method as in the forty-second non-limiting example wherein the first medical device is further operatively coupled to a third electrode and the first and second electrodes form a first sensing bipole adapted for atrial sensing, and the third electrode forms, with one of the first or second electrodes, a second sensing bipole adapted for atrial sensing.

Additionally or alternatively a forty-ninth non-limiting example takes the form of a method as in the fortieth non-limiting example further comprising determining propagation of the P-wave using the first and second bipoles, observing an amplitude of the P-wave using the second medical device, and confirming detection of the P-wave based on the propagation and the amplitude using the second medical device.

A fiftieth non-limiting example takes the form of an IMD comprising a housing a first lead external to the housing and adapted for placement in an ITV of a patient, the first lead including a distal portion that includes a sensing bipole adapted for atrial sensing, and a proximal portion having a proximal end that includes a connector for coupling to the housing, operational circuitry disposed within the housing and operatively coupled to the first lead, the operational circuitry including sensing circuitry configured to analyze atrial signals from the sensing bipole adapted for atrial sensing and identify a P-wave signal, a power source disposed within the housing, operatively coupled to the operational circuitry, and configured to power the operational circuitry.

Additionally or alternatively a fifty-first non-limiting example takes the form of an IMD as in the fiftieth non-limiting example the operational circuitry further including communication circuitry configured for communicative coupling to a second medical device, and processing circuitry configured to analyze the P-wave signal and cause the communication circuitry to communicate pacing therapy directions to the second medical device based on the analysis of the P-wave signal.

Additionally or alternatively a fifty-second non-limiting example takes the form of an IMD as in the fifty-first non-limiting example and a leadless cardiac pacemaker (LCP) for placement in, on or adjacent to the heart, wherein the LCP is configured as the second medical device to which the communication circuitry of the IMD, and the LCP is configured to deliver pacing therapy using the pacing therapy directions.

Additionally or alternatively a fifty-third non-limiting example takes the form of an IMD as in the fifty-second non-limiting example wherein the LCP is configured for placement in or on the right ventricle of the heart, and the processing circuitry is configured to tailor the pacing therapy directions for pacing delivered from the right ventricle.

Additionally or alternatively a fifty-fourth non-limiting example takes the form of an IMD as in the fifty-second non-limiting example wherein the LCP is configured for placement in or on the left ventricle of the heart, and the processing circuitry is configured to tailor the pacing therapy directions for pacing delivered from the left ventricle.

Additionally or alternatively a fifty-fifth non-limiting example takes the form of an IMD as in the fifty-second non-limiting example wherein the processing circuitry is configured to tailor the pacing therapy directions for cardiac resynchronization therapy.

Additionally or alternatively a fifty-sixth non-limiting example takes the form of an IMD as in the fifty-second non-limiting example wherein the processing circuitry is configured to tailor the pacing therapy directions for Vdd pacing.

Additionally or alternatively a fifty-seventh non-limiting example takes the form of an IMD as in the fiftieth non-limiting example wherein the IMD is an implantable defibrillator and the first lead includes a defibrillation coil at a first location on the distal portion of the first lead, with the sensing bipole including at least two electrodes distal of the defibrillation coil on the first lead.

Additionally or alternatively a fifty-eighth non-limiting example takes the form of an IMD as in the fiftieth non-limiting example wherein the IMD is an implantable defibrillator further comprising a second lead having a defibrillation coil disposed thereon, the second lead adapted for placement subcutaneously or in a substernal location.

Additionally or alternatively a fifty-ninth non-limiting example takes the form of an IMD as in the fiftieth non-limiting example wherein the first lead comprises first, second and third electrodes, the first and second electrodes forming a first sensing bipole adapted for atrial sensing, and the third electrode forming, with one of the first or second electrodes, a second sensing bipole adapted for atrial sensing.

Additionally or alternatively a sixtieth non-limiting example takes the form of an IMD as in the fifty-ninth non-limiting example wherein the operational circuitry is further configured to determine propagation of the P-wave signal using the first and second bipoles, observe an amplitude of the P-wave signal, and confirm detection of the P-wave signal based on the propagation and the amplitude.

Additionally or alternatively a sixty-first non-limiting example takes the form of an IMD as in the fiftieth non-limiting example wherein the first lead is further adapted for placement in an intercostal vein of the patient.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3 illustrates a torso in a section view;

FIG. 5C illustrates an implantable defibrillator and a leadless cardiac pacemaker (LCP);

DETAILED DESCRIPTION

Figure 1:
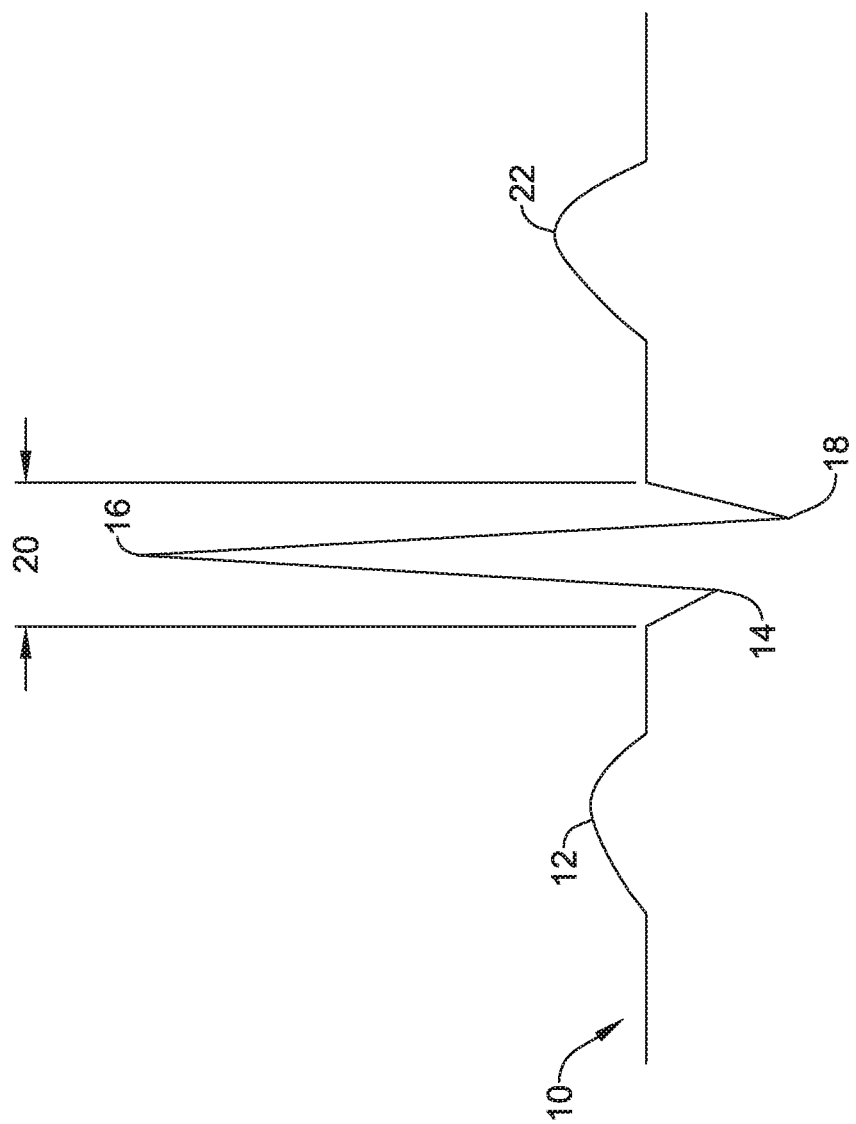
FIG. 1 illustrates a cardiac signal.

FIG. 1 shows an illustrative cardiac signal. The trace 10 is marked using standard convention with the P-wave 12, R-wave 16 (which, when combined with preceding Q-wave 14 and following S-wave 18 may be referred to as the QRS complex 20), and later T-wave 22. The P-wave 12 represents atrial depolarization associated with atrial contraction to load the ventricles, the R-wave 16 or QRS complex 20 represents ventricular depolarization associated with the ventricles contracting to pump blood to the body and lungs, and the T-wave 22 is associated with the electrical activity that repolarizes the ventricular muscle in preparation for a next beat. With heart failure and/or dysynchrony, the timing of these individual events may be anomalous or abnormal, and the shape of depolarization waves can be different from that shown as by, for example, having a much wider QRS complex 20 or R-wave 16.

Sensing of atrial depolarizations (i.e., P-waves 12) may be useful to control electrical therapies of pacemakers and implantable cardioverter-defibrillators (ICDs). When a depolarization wave passes an electrode of a cardiac lead, a deflection in an electrogram signal may travel up the lead wire to the pacemaker or ICD, where a sensing system may amplify, filter, digitize, and process the signal. A detected event may occur when the sensing system determines that an atrial depolarization has occurred.

Appropriate detection may result when one detected event corresponds to one depolarization wave. Failure to sense a depolarization wave may result in undersensing. Underdetection may occur when the depolarization wave has insufficient amplitude or frequency content to be recognized as a sensed event. Overdetection may occur when nonphysiologic signals or physiologic signals that do not reflect atrial depolarization are sensed, or if one depolarization wave is detected twice. Overdetection and underdetection may lead to misdiagnosis and/or inappropriate therapy delivery or failure to deliver appropriate therapy.

Pacing leads having at least two electrodes at a distal end may be used for bipolar pacing from an attached implantable pulse generator (IP(I) or ICD, as well as for providing atrial sensing information to the ICD. According to various embodiments, the design and proximity of the leads can be such as to enhance the electrical signal sensing capability of the leads to allow recognition and discrimination of the sensed signals.

The internal thoracic vein (ITV), which may also be referred to as the internal mammary vein, is a vessel that drains the chest wall and breasts. There are both left and right internal thoracic veins on either side of the sternum, beneath the ribs. The ITV arises from the superior epigastric vein and musculophrenic vein, accompanies the internal thoracic artery along its course and terminates in the brachiocephalic vein. The present inventors have recognized that the ITV may make a suitable location for placement of a cardiac lead for electrical signal sensing capability to allow recognition and discrimination of atrial activity. While much of the following disclosure focuses on the use of the ITV, many of these concepts could also be applied to the internal thoracic arteries, which may sometimes be referenced as the internal mammary arteries. Some additional details related to the use of the ITV for placement of cardiac leads may be found in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference. In the Ser. No. 15/667,167 patent application, some examples include methods of implanting a lead for use in a cardiac stimulus system, the lead having at least one electrode; the method comprising inserting the lead into the ITV to a desired location relative to the heart of a patient. In one such example, the method includes accessing a brachiocephalic vein of the patient and advancing a distal portion of the lead into the ITV from the brachiocephalic vein. In a further version, the step of establishing access to the brachiocephalic vein comprises inserting an introducer sheath into one of the axillary, jugular, cephalic or subclavian veins of the patient and advancing at least the lead through the introducer sheath, into the brachiocephalic vein. In another example, the method instead accessing, with a needle or by cut down, one of the ITV through an intercostal space between two ribs; and advancing the distal end of the lead into the ITV.

Figure 2:
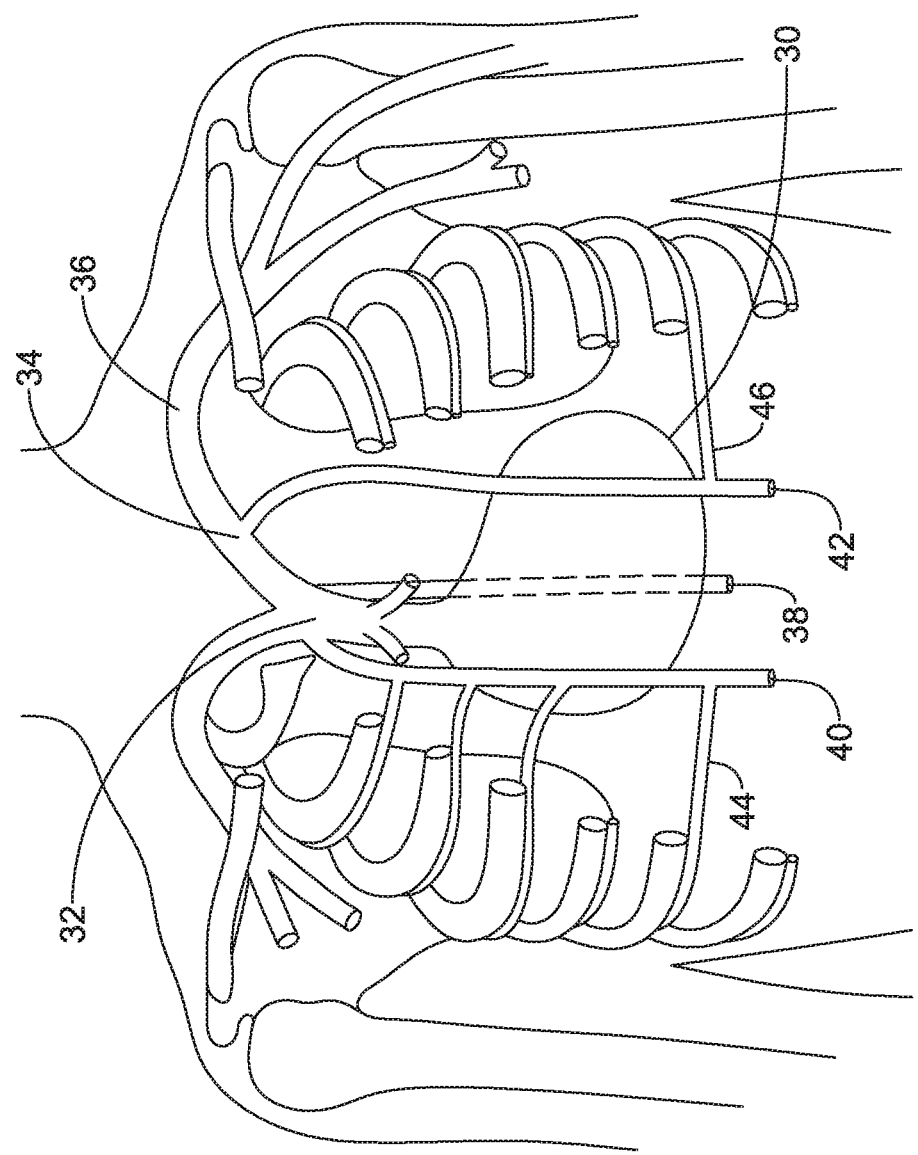
FIG. 2 illustrates a thoracic anatomy including the internal thoracic veins (ITVs)

FIG. 2 illustrates the thoracic anatomy including location of the internal thoracic veins (ITVs) 40, 42. A right intercostal vein 44 may couple to the right ITV 40 and a left intercostal vein 46 may couple to the left ITV 42. The right and left intercostal veins 44, 46 may each run along a costal groove on an inferior portion of a rib. An outline of the heart is shown at 30, with the superior vena cava (SVC) shown at 32. The brachiocephalic veins 34 couple to the SVC 32 and extend past various cephalic branches to the subclavian vein 36. The azygos vein is also shown at 38.

As used herein, the "ITV" is the name applied for the vein while it runs beneath the chest, that is, superior to the lower margin of the ribs. Near the lower margin of the ribs, the musculophrenic vein branches off from the ITV going laterally along the lower rib margin. Inferior of this location, the blood vessel is referred to (at least in this description) as the superior epigastric vein.

FIG. 3 shows the torso in a section view to highlight the location of various vascular structures. More particularly, in the example, the left and right ITV are shown at 50, 52, running parallel to and more central of the internal thoracic arteries 54, 56, on either side of the sternum 58. The heart is shown at 60, with the lungs at 62 and spinal column at 64. The ITV 50, 52 lie beneath the ribs but outside and separate from the pleurae of lungs 62. The ribs are omitted in the drawing in order to show the intercostal veins. The left anterior intercostal vein 68 runs along the inferior portion of a rib and couples to the left ITV 50 at junction 70, forming an ostium at the point where the left anterior intercostal vein 68 flows into the left ITV 50. Additionally, the right intercostal vein 72 runs along the inferior portion of another rib and couples to the right ITV 52 at junction 74, forming an ostium at the point where the anterior intercostal vein 72 flows into the right ITV 52.

An azygos vein and a hemiazygos vein are shown at 76, 78, running parallel to and on either side, more or less, of the spinal column 64. The azygos vein 76 and the hemiazygos vein 78 also lie beneath the ribs but outside and separate from the pleurae of lungs 62. The left posterior intercostal vein 86 couples to the hemiazygos vein 78 at a junction 82, forming an ostium at the point where the intercostal vein 86 flows into the hemiazygos vein 78. Additionally, the right posterior intercostal vein 84 couples to the azygos vein 76 at a junction 80, forming an ostium at the point where the intercostal vein 86 flows into the azygos vein 76.

Figure 4B:
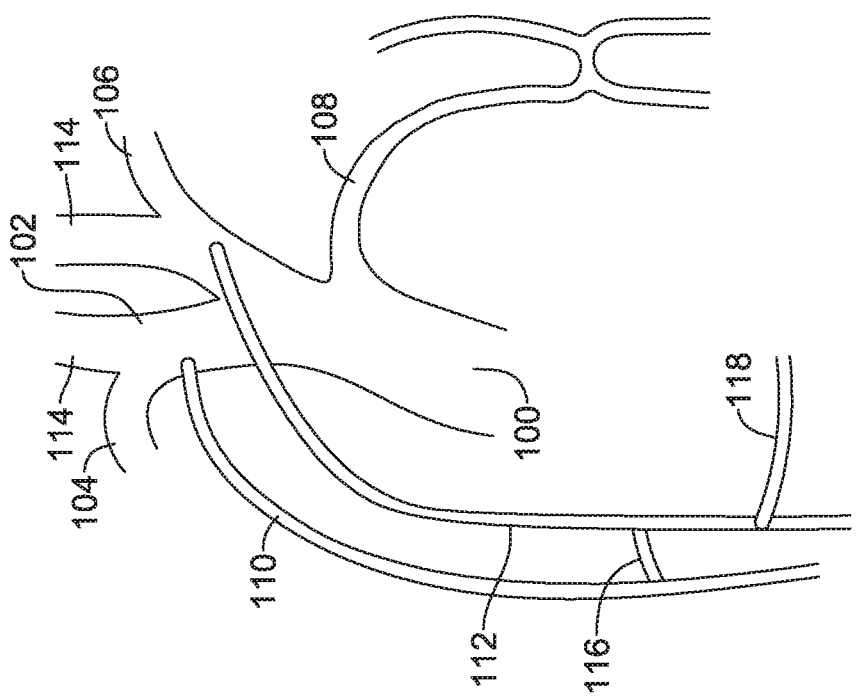
FIG. 4A-4B illustrates the ITV and linked vasculature in isolation.
Figure 4A:
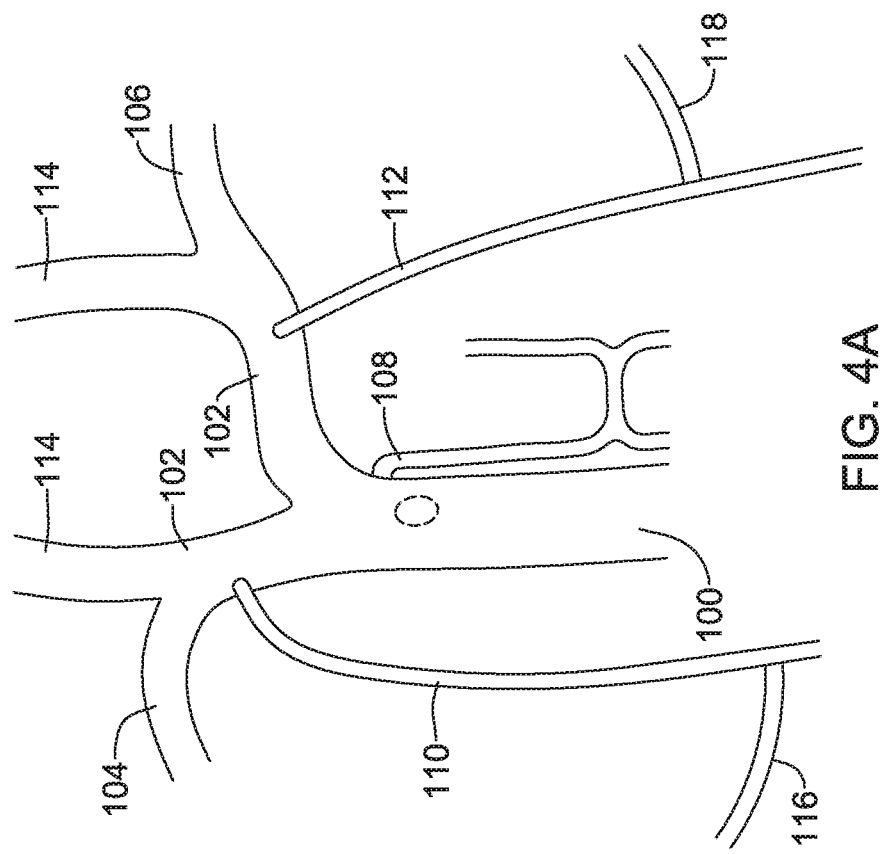

FIGS. 4A-4B show the ITV and linked vasculature in isolation. FIG. 4A is an anterior view of selected portions of the venous structure of the upper torso, and FIG. 4B is a lateral view of the same. The SVC is shown at 100, with the brachiocephalic veins 102 splitting at the upper end of the SVC. The right subclavian vein is at 104, and the left subclavian vein is at 106. The azygos vein is included in the illustration at 108, extending off the posterior of the SVC 100, and running inferiorly posterior of the heart as can be understood from the lateral view of FIG. 4B.

The right and left ITV are shown at 110, 112. These each branch off at a location that is considered part of the brachiocephalic veins 102. Selected right and left intercostal veins are shown at 116, 118. There are left and right intercostal veins along the lower margin of each of the ribs. In several embodiments the intercostal veins of the $4^{th}$, $5^{th}$, or $6^{th}$ ribs are proposed for implantation of a lead with access through the intercostal vein to the ITV. In one example, the intercostal vein of the $6^{th}$ rib is accessed. In other examples, access may be more superior or inferior than these locations, as desired. These may branch off at a location of the right and left ITV's and continue to run along a costal groove of an inferior portion of a the ribs. The internal jugular veins are also shown at 114.

Figure 5A:
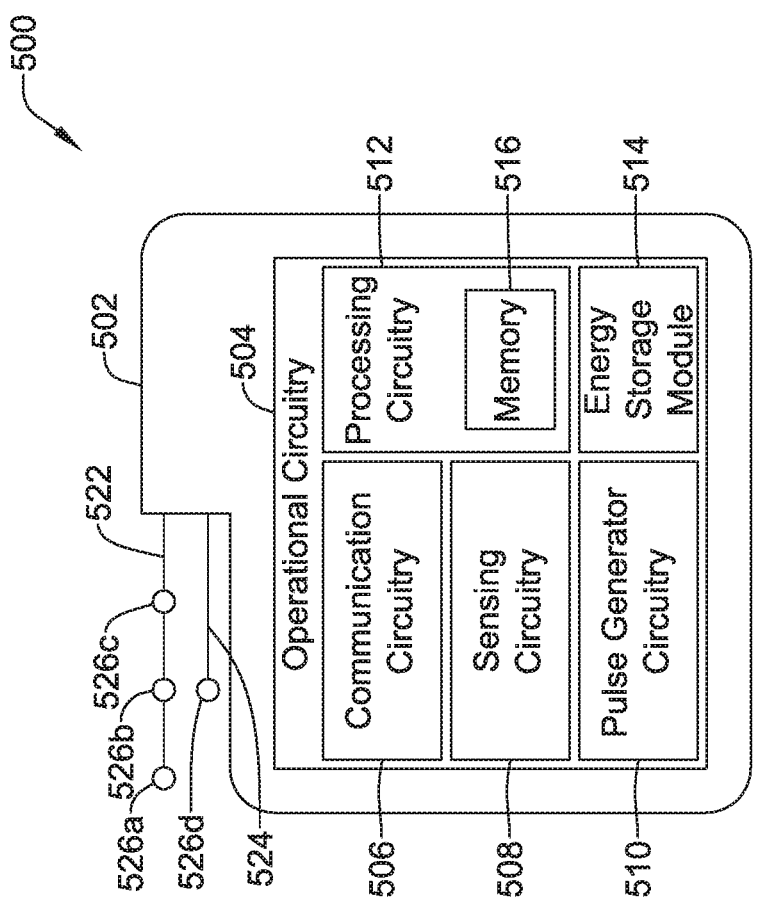
FIG. 5A illustrates an implantable medical device (IMD)

FIG. 5A depicts an illustrative implantable medical device (IMD) 500 that may be implanted into a patient and may operate to deliver appropriate therapy to the heart. For example, the IMD 500 may be a therapeutic device (e.g., an implantable defibrillator, an implantable pulse generator, etc.), a diagnostic device, a cardiac stimulator, a neural stimulator. In certain embodiments, the IMD 500 may be configured to sense cardiac electrical signals (e.g., R-waves and/or P-waves), determine occurrences of tachyarrhythmias based on the sensed signals, and may be configured to deliver defibrillation therapy in response to determining an occurrence of a tachyarrhythmia.

As can be seen in FIG. 1, the IMD 500 may have a housing 502 that encases operational circuitry 504. In certain embodiments, the housing 502 may be implanted in, for example, a thoracic region of the patient. The housing 502 may generally include any of a number of known materials that are safe for implantation in a human body and may, when implanted, hermetically seal the various components of the IMD 500 from fluids and tissues of the patient's body. Furthermore, in some examples, the IMD 500 may also include a header for securing leads 522 and 524.

In various embodiments, the leads 522, 524 may include electrical wires that conduct electrical signals between electrodes 526A-526D and one or more circuits located within the housing 502. In some cases, the leads 522, 524 may be connected to and extend away from the housing 502 of the IMD 500. In some examples, the leads 522, 524 are implanted on, within, or adjacent to a heart of a patient. In some examples, the leads 522 and/or 524 may be located in the ITV and/or in an intercostal vein of a patient. In some cases, the one or more of the electrodes 526A-526D may be positioned subcutaneously and outside of the patient's heart (e.g., in an ITV and/or an intercostal vein).

The leads 522, 524 may contain one or more electrodes 526A-526D positioned at various locations on the leads 522, 524, and in some cases at various distances from the housing 502. Some leads (e.g. 524) may only include a single electrode (e.g., 526D), while other leads (e.g., 522) may include multiple electrodes (e.g., 526A-526C). Generally, the electrodes 526A-526D are positioned on the leads 522, 524 such that when the leads 522, 524 are implanted within the patient, one or more of the electrodes 526A-526D are positioned to perform a desired function.

In some examples, the electrodes 526A-526D may be configured to create a sensing bipole adapted for atrial sensing (e.g., P-wave sensing) or for ventricular sensing (R-wave or QRS complex sensing). For example, the electrode 526A may form a first sensing bipole with the electrode 526B, the electrode 526A may form a second sensing bipole with the electrode 526C, and the electrode 526B may form a third sensing bipole with the electrode 526C. In some cases, the electrodes 526A-526D may conduct intrinsically generated electrical signals to the leads 522, 524, e.g. signals representative of intrinsic cardiac electrical activity (e.g., P-waves). The leads 522, 524 may, in turn, conduct the received electrical signals to the operational circuitry 504 of the IMD 500. The operational circuitry 504 may then perform operations based on the received electrical signals. For instance, continuing with our example of the first, second, and third sensing bipoles, the operational circuitry 504 may be configured to determine signal propagation of the P-wave using the first, second, and/or third bipoles.

In some cases, the IMD 500 may generate electrical stimulation signals, and the leads 522, 524 may conduct the generated electrical stimulation signals to the electrodes 526A-526D. The electrodes 526A-526D may then conduct the electrical signals and deliver the signals to the patient's heart (either directly or indirectly). The electrodes 526A-526D may take the form of ring electrodes, segmented electrodes, coil electrodes, or other designs. One or more transducers, such as a transducer to sense optical or mechanical (sound or motion) signals may be provided in addition to or in place of the electrodes 526A-526D. The housing 502 may serve as an electrode for sensing purposes as well.

In various embodiments, the operational circuitry 504 may include communication circuitry 506, sensing circuitry 508, pulse generator circuitry 510, processing circuitry 512, an energy storage module 514, and memory 516. The IMD 500 may include more or less circuitry and modules, depending on the application. For example, sensing circuitry 508 may include input switches to select one or more sensing bipoles or vectors for use in cardiac signal sensing (atrial or ventricular), and may have filtering, amplification and analog-to-digital conversion circuitry to provide a signal to the processing circuitry 512. Dedicated circuits may be provided to perform specific functions such as atrial or ventricular event detection and/or morphology analysis in the sensing circuitry 508. Processing circuitry 512 may use instruction sets stored in the memory 516 to perform various analyses described below and to control system operation.

In certain embodiments, the communication module 506 may be configured to communicate with devices such as sensors, other medical devices such as a leadless cardiac pacemaker (LCP), a subcutaneous implantable cardioverter defibrillator (S-ICD), an implantable pulse generator (IPG), and/or the like, that are located externally to the IMD 500. Such devices may be located either external or internal to the patient's body. Irrespective of the location, external devices (i.e. external to the IMD 500 but not necessarily external to the patient's body) can communicate with the IMD 500 via communication circuitry 506 to accomplish one or more desired functions. For example, the IMD 500 may communicate information, such as sensed electrical signals, data, instructions, messages, P-wave detection markers, etc., to an external medical device (e.g. LCP and/or programmer) through the communication circuitry 506. The external medical device may use the communicated signals, data, instructions, messages, P-wave detection markers, etc., to perform various functions, such as determining occurrences of arrhythmias, delivering electrical stimulation therapy, storing received data, and/or performing any other suitable function. The IMD 500 may additionally receive information such as signals, data, instructions and/or messages from the external medical devices through the communication circuitry 506, and the IMD 500 may use the received signals, data, instructions and/or messages to perform various functions, such as determining occurrences of arrhythmias, delivering electrical stimulation therapy, storing received data, and/or performing any other suitable function. The communication circuitry 506 may be configured to use one or more methods for communicating with external devices. For example, the communication circuitry 506 may communicate via radiofrequency (RF) signals (Bluetooth, ISM, or Medradio, for example), inductive coupling, optical signals, acoustic signals, conducted communication signals, and/or any other signals suitable for communication.

In some examples, the sensing circuitry 508 may be configured to sense the cardiac electrical activity of the heart. For example, the sensing circuitry 508 may be connected to the electrodes 526A-526D, and the sensing circuitry 508 may be configured to receive cardiac electrical signals conducted through the electrodes 526A-526D. In some cases, the cardiac electrical activity may be atrial signals and the sensing circuitry 508 may be configured to sense the P-waves from the atrial signals. For instance, the lead 522 may be located in the ITV and/or the intercostal vein of a patient. Electrodes 526A and 526B may form a sensing bipole adapted for atrial sensing of the heart from the ITV and/or the intercostal vein. The sensing circuitry 508 may then analyze the atrial signals and observe the P-waves from the atrial signals captured using the sensing bipole. Additional or other sensing bipoles may be selected and used for other purposes such as R-wave sensing/detection and QRS morphology analysis, as desired. In some cases, the sensing circuitry 508 may work in conjunction with the processing circuitry 512 in analyzing cardiac electrical activity of the heart.

In the example shown in FIG. 5A, the pulse generator circuitry 510 may be electrically connected to the electrodes 526A-526D. The pulse generator circuitry 510 may be configured to generate electrical stimulation signals. For example, the pulse generator circuitry 510 may generate and deliver electrical stimulation signals by using energy stored in the energy storage module 514 and deliver the generated electrical stimulation signals via the electrodes 526A-526C and/or 526D. Alternatively, or additionally, the pulse generator circuitry 510 may include one or more capacitors, and the pulse generator circuitry 510 may charge the one or more capacitors by drawing energy from the energy storage module 514. The pulse generator circuitry 510 may then use the energy of the one or more capacitors to deliver the generated electrical stimulation signals via the electrodes 526A-526C and/or 526D. In at least some examples, the pulse generator circuitry 510 may include switching circuitry to selectively connect one or more of the electrodes 526A-526D and/or sensing bipoles to the pulse generator circuitry 510 in order to select which sensing bipoles from the electrodes 526A-526D (and/or other electrodes) the pulse generator circuitry 510 delivers the electrical sensing and/or stimulation therapy. An H-Bridge is one known circuit for therapy output control. The pulse generator circuitry 510 may generate and deliver electrical stimulation signals with particular features or in particular sequences in order to provide one or multiple of a number of different stimulation therapies. For example, the pulse generator circuitry 510 may be configured to generate electrical stimulation signals to provide electrical stimulation therapy to combat bradycardia, tachyarrhythmias, atrial or ventricular fibrillation and/or to produce any other suitable electrical stimulation therapy such as cardiac resynchronization therapy (CRT). Some more common electrical stimulation therapies include anti-tachycardia pacing (ATP) therapy, CRT, and cardioversion/defibrillation therapy. In some cases, the pulse generator circuitry 510 may provide a controllable pulse energy. In some cases, the pulse generator circuitry 510 may allow the processing circuitry 512 to control the pulse voltage, current, pulse width, pulse shape or morphology, and/or any other suitable pulse characteristic.

The processing circuitry 512 may be configured to control the operation of the IMD 500. For example, the processing circuitry 512 may be configured to receive electrical signals from the sensing circuitry 508. Based on the received signals, the processing circuitry 512 may determine, for example, abnormalities in the operation of the heart. Based on any determined abnormalities, the processing circuitry 512 may control the pulse generator circuitry 510 to generate and deliver electrical stimulation in accordance with one or more therapies to treat the determined abnormalities. The processing circuitry 512 may further control the communication circuitry 506 to send electrical stimulation directions in accordance with one or more therapies to treat the determined abnormalities to other devices. The other devices may then generate and deliver the electrical stimulation in accordance with the directions. In some examples, the processing circuitry 512 may control the communication circuitry 506 to receiver information from another device. The processing circuitry 512 may then use such received information to help determine whether an abnormality is occurring, determine a type of abnormality, and/or to take particular action in response to the information.

In some examples, the processing circuitry 512 may include a pre-programmed chip, such as a very-large-scale integration (VLSI) chip and/or an application specific integrated circuit (ASIC). In such embodiments, the chip may be pre-programmed with control logic in order to control the operation of the IMD 500. For example, a state machine architecture may be used. By using a pre-programmed chip, the processing circuitry 512 may use less power than other programmable circuits (e.g. general purpose programmable microprocessors) while still being able to maintain basic functionality, thereby potentially increasing the battery life of the IMD 500.

In other examples, the processing circuitry 512 may include a programmable microprocessor. Such a programmable microprocessor may allow a user to modify the control logic of the IMD 500 even after implantation, thereby allowing for greater flexibility of the IMD 500 than when using a pre-programmed ASIC. In some examples, the processing circuitry 512 may further include a memory 516, and the processing circuitry 512 may store information on and read information from the memory 516. In other examples, the IMD 500 may include a separate memory (not shown) that is in communication with the processing circuitry 512, such that the processing circuitry 512 may read and write information to and from the separate memory.

The energy storage module 514 may provide power to the IMD 500 for its operations. In some instances, the energy storage module 514 may be a rechargeable battery, which may help increase the useable lifespan of the IMD 500. In still other examples, the energy storage module 514 may be some other type of power source such as a primary cell battery, as desired.

Figure 5B:
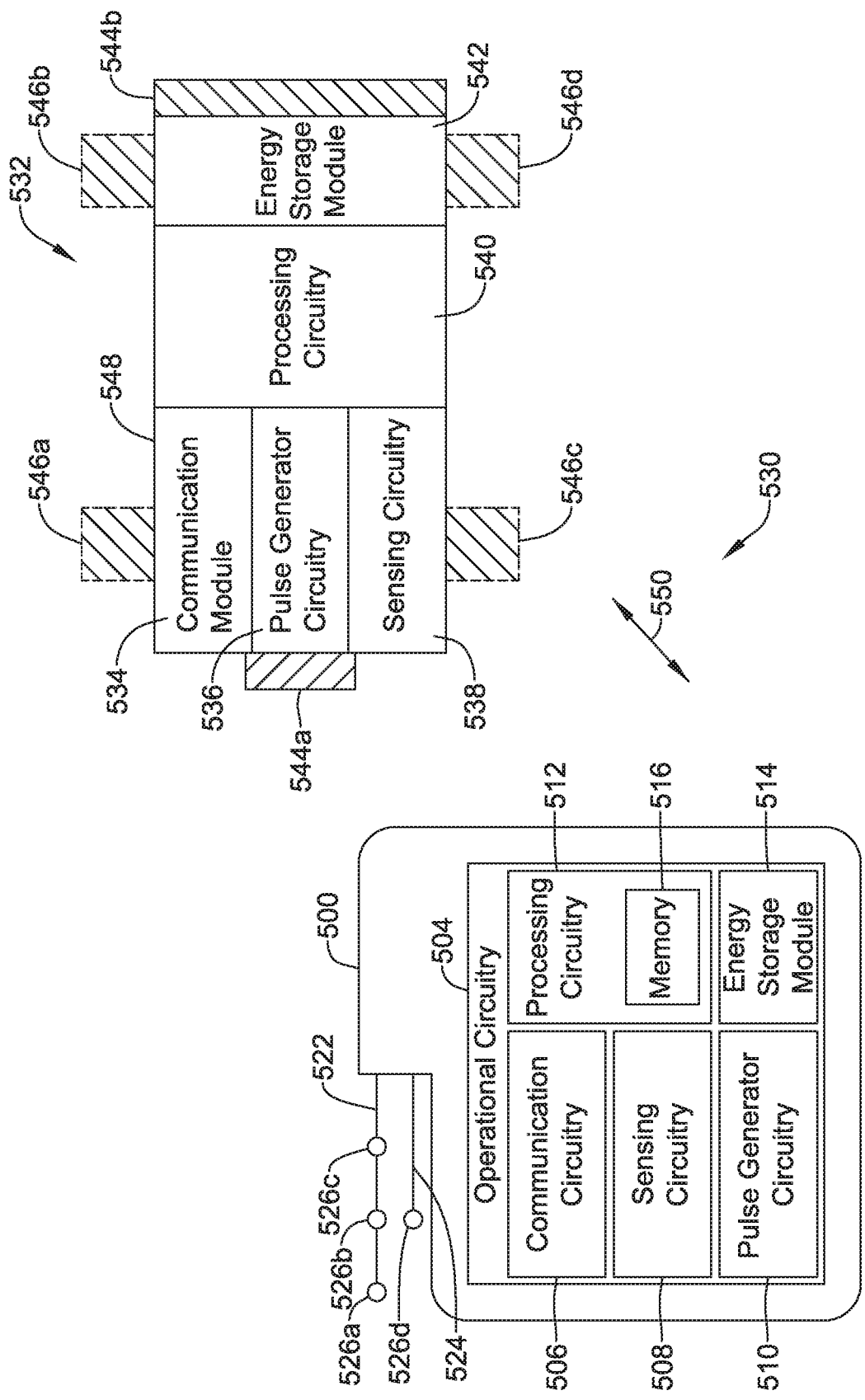
FIG. 5B illustrates an implantable system.

FIG. 5B depicts an example of an implantable system 530 that may be implanted into a patient and may operate to deliver appropriate therapy to the heart. In various embodiments, the system 530 may include a medical device (MD) 532, which may be used in conjunction with the IMD 500 in order to detect and/or treat cardiac abnormalities. In some cases, the MD 532 may be considered as an example of an LCP, IPG, and/or an S-ICD. In the example shown, the MD 532 may include communication circuitry 534, pulse generator circuitry 536, sensing circuitry 538, processing circuitry 540, and an energy storage module 542. Each of these circuitries may be similar to the circuitries 506, 508, 510, 512, and 514 of the IMD 500. Additionally, the energy storage module 542 may be similar to the energy storage module 514 of the IMD 500. In some examples, however, the MD 532 may have a smaller volume within a housing 544. In such examples, the MD 532 may include a smaller battery and/or smaller processing circuitry 540 capable of using less power to help extend the lifetime of the MD 532.

In the example shown in FIG. 5B, the pulse generator circuitry 536 may be electrically connected to the electrodes 544A and 544B. In some examples, the MD 532 may additionally include electrodes 546A-546D. In such examples, the pulse generator circuitry 536 may also be electrically connected to the electrodes 546A-546D and deliver generated electrical stimulation signals via the electrodes 544A, 544B and/or 546A-546D. In at least some examples, the pulse generator circuitry 536 of the MD 532 may include switching circuitry to selectively connect one or more of the electrodes 544A, 544B and/or 546A-546D to the pulse generator circuitry 536 in order to select which of the electrodes (and/or other electrodes) the pulse generator circuitry 536 delivers the electrical stimulation therapy. The pulse generator circuitry 536 may generate and deliver electrical stimulation signals with particular features or in particular sequences in order to provide one or multiple of a number of different stimulation therapies.

The electrodes 544A, 544B and 546A-546D can be secured relative to the housing 548 but exposed to the tissue and/or blood surrounding the MD 532. In some cases, the electrodes 544A, 544B may be generally disposed on either end of the MD 532 and may be in electrical communication with one or more of the circuitries 534, 536, 538, and 540. The electrodes 544A, 544B and 546A-546D may be supported by the housing 548, although in some examples, the electrodes 544A, 544B and 546A-546D may be connected to the housing 548 through short connecting wires such that the electrodes 544A, 544B and 546A-546D are not directly secured relative to the housing 548. In examples where the MD 532 includes one or more electrodes 546A-546D, the electrodes 546A-546D may in some cases be disposed on the sides of the MD 532, which may increase the number of electrodes by which the MD 532 may sense cardiac electrical activity, deliver electrical stimulation and/or communicate with an external medical device. The electrodes 544A, 544B and 546A-546D can be made up of one or more biocompatible conductive materials such as various metals or alloys that are known to be safe for implantation within a human body. In some instances, the electrodes 544A, 544B and/or 546A-546D connected to the MD 532 may have an insulative portion that electrically isolates the electrodes 544A, 544B and 546A-546D from adjacent electrodes, the housing 548, and/or other parts of the second MD 532. In some cases, one or more of the electrodes 544A, 544B and 546A-546D may be provided on a tail (not shown) that extends away from the housing 548.

FIG. 5B also illustrates an example of the implantable system 530 and a communication pathway 550 through which the IMD 500 the MD 532 may communicate. According to various embodiments, other external devices (not shown in FIG. 5B) may also use the communication pathway 550 to communicate with the IMD 500, the MD 532, or both. In some cases, other external devices may include an external programmer device that may be used to program one or more devices of the system 530. The IMD 500 and the MD 532 may use the communication pathway 550 to perform several functions. For example, the IMD 500 may sense intrinsic cardiac electrical signals and may communicate such signals to the MD 532 via the communication pathway 550. In one example, the IMD 500 may receive atrial cardiac signals, analyze the P-wave signals from the atrial cardiac signals, and determine an occurrence of an arrhythmia. In some cases, the IMD 500 may communicate such determinations to the MD 532. In some cases, the MD 532 and/or the IMD 500 may take action based on the communicated determination of an arrhythmia, such as by delivering a suitable electrical stimulation to the heart of the patient.

It is contemplated that the communication pathway 550 may communicate using RF signals, inductive coupling, optical signals, acoustic signals, or any other signals suitable for communication. Additionally, in at least some examples, the communication pathway 550 may include multiple signal types. For instance, the IMD 500 may communicate with the MD 532 using a first signal type (e.g. conducted communication) but communicate with external devices using a second signal type (e.g. RF communication). Further, in some examples, communication between devices may be limited. For instance, as described above, in some examples, the IMD 500 may communicate with the MD 532 only through other sensors/devices, where the IMD 500 sends signals to other sensors/devices, and other sensors/devices relay the received signals to the MD 532.

In some cases, the communication pathway 550 may include conducted communication. Accordingly, devices of the system 530 may have components that allow for such conducted communication. For instance, the devices of system 530 may be configured to transmit conducted communication signals (e.g. current and/or voltage pulses) into the patient's body via one or more electrodes of a transmitting device, and may receive the conducted communication signals (e.g. pulses) via one or more electrodes of a receiving device. The patient's body may "conduct" the conducted communication signals (e.g. pulses) from the one or more electrodes of the transmitting device to the electrodes of the receiving device in the system 530. In such examples, the delivered conducted communication signals (e.g. pulses) may differ from pacing or other therapy signals. For example, the devices of the system 530 may deliver electrical communication pulses at an amplitude or pulse width chosen to avoid stimulating the patient's heart or other tissue, and which is below a perception threshold of the patient's nervous system. In some examples, communication may be delivered during a refractory period of the heart to avoid stimulation of the heart. Avoidance of stimulation and/or perception are preferable but may not be necessary. In some examples, a communication signal may be applied over top of a therapy signal such as by incorporating a communication pattern in a pace therapy pulse.

Delivered electrical communication pulses may be modulated in any suitable manner to encode communicated information. In some cases, the communication pulses may be pulse width modulated or amplitude modulated. Alternatively, or in addition, the time between pulses may be modulated to encode desired information. In some cases, conducted communication pulses may be voltage pulses, current pulses, biphasic voltage pulses, biphasic current pulses, or any other suitable electrical pulse as desired.

FIG. 5C depicts an illustrative implantable defibrillator 600 and an illustrative LCP 602. In various embodiments, the implantable defibrillator 600 may be an example of the IMD 500. In such examples, the implantable defibrillator 600 may include a housing 604 having operational circuitry (e.g., operational circuitry 504, from FIG. 5A) disposed within. Additionally, one or more leads 606 and 608, similar to leads 522 and 524, may be connected to the operational circuitry and extend away from the housing 604.

In certain embodiments, the lead 606 may include a bipolar sensing electrode pair 616 at a distal end 610 adapted for atrial sensing. In some cases, the bipolar sensing pair 616 may include tip electrode 618A and electrode 618B spaced proximally away from the electrode 618A. In other cases, the bipolar sensing pair 616 may include the tip electrode 618A and electrode 618C spaced proximally away from the electrode 618A. In other cases, the bipolar sensing pair 616 may include the electrode 618B and the electrode 618C. In yet further embodiments, the lead 606 may have two or three bipolar sensing electrode pairs 616 that include two or three combinations of the electrodes 618A-618C. In some examples, the lead 606 may also include a defibrillation coil 620A and the bipolar sensing electrode pair 616 may be spaced distally away from the defibrillation coil 620A.

In various embodiments, the implantable defibrillator 600 may also include the lead 608. In some examples, the lead 608 may also include a defibrillation coil 620B at a distal end 614. As illustrated in FIG. 5C, the electrodes 620A, 620B are coil electrodes. However, other types of electrodes, for example, plural interconnected ring electrodes, may also be employed. In some examples, the lead 606 may have a proximal end 612 that includes a proximal connector 622 configured to attach the lead 606 to the housing 604 and couple the electrodes 618A-618C and 620A to the internal circuitry (i.e., the operational circuitry) of the implantable defibrillator 600. Furthermore, the lead 608 may have a proximal end 616 that includes a proximal connector 624 configured to attach the lead 608 to the housing 604 and couple the electrode 620B to the operational circuitry of the implantable defibrillator 600. In certain embodiments, the leads 606, 608 may also include a hollow interior extending from the proximal ends 612, 606 to the distal ends 610, 614. The hollow interior may allow for the introduction of a stylet (not shown) during implant, which may allow the leads 606, 608 to be guided through a point of venous insertion to an implant site (e.g., an ITV and an intercostal vein).

In various embodiments, the LCP 602 may be similar in form and function to the MD 532, described with respect to FIG. 5B. The LCP 602 may include any of the circuitries, modules, and/or structural features described above with respect to the MD 532 and may operate to deliver appropriate therapy to the heart, such as to deliver anti-tachycardia pacing (ATP) therapy, cardiac resynchronization therapy (CRT), bradycardia therapy, Vdd pacing and/or the like.

The LCP 602 may include a shell or housing 626 having a proximal end 628 and a distal end 630. The illustrative LCP 602 includes a first electrode 632 secured relative to the housing 626 and positioned adjacent to the distal end 630 of the housing 626 and a second electrode 634 secured relative to the housing 626 and positioned adjacent to the proximal end 628 of the housing 626. In some cases, the housing 626 may include a conductive material and may be insulated along a portion of its length. A section along the proximal end 628 may be free of insulation so as to define the second electrode 634. The electrodes 632, 634 may be sensing and/or pacing electrodes to provide electro-therapy and/or sensing capabilities. The first electrode 632 may be capable of being positioned against or may otherwise contact the cardiac tissue of the heart while the second electrode 634 may be spaced away from the first electrode 632. The first and/or second electrodes 632, 634 may be exposed to the environment outside the housing 626 (e.g. to blood and/or tissue).

In some cases, the LCP 602 may include pulse generator circuitry (e.g., electrical circuitry) and an energy storage module (e.g., a battery) within the housing 626 to provide electrical signals to the electrodes 620, 622 to control the pacing/sensing electrodes 620, 622. While not explicitly shown, the LCP 602 may also include, communications circuitry, sensing circuitry, and processing circuitry, similar in form and function to the circuitries 534, 536, 538, and 540 described above. The various modules and electrical circuitry may be disposed within the housing 626. Electrical connections between the circuitries and the electrodes 632, 634 may allow electrical stimulation to heart tissue and/or sense a physiological condition.

In the example shown, the LCP 602 includes a fixation mechanism 636 proximate the distal end 630 of the housing 626. The fixation mechanism 636 may be configured to attach the LCP 602 to a wall of the heart, or otherwise anchor the LCP 602 to the anatomy of the patient. In some instances, the fixation mechanism 636 may include one or more, or a plurality of hooks or tines 636 anchored into the cardiac tissue of the heart to attach the LCP 602 to a tissue wall. In other instances, the fixation mechanism 636 may include one or more, or a plurality of passive tines, configured to entangle with trabeculae within the chamber of the heart and/or a helical fixation anchor configured to be screwed into a tissue wall to anchor the LCP 602 to the heart. These are just examples.

The LCP 602 may further include a docking member 638 proximate the proximal end 628 of the housing 626. The docking member 638 may be configured to facilitate delivery and/or retrieval of the LCP 602. For example, the docking member 638 may extend from the proximal end 628 of the housing 626 along a longitudinal axis of the housing 626. The docking member 638 may include a head portion 640 and a neck portion 642 extending between the housing 626 and the head portion 640. The head portion 640 may be an enlarged portion relative to the neck portion 642. For example, the head portion 640 may have a radial dimension from the longitudinal axis of the LCP 602 that is greater than a radial dimension of the neck portion 642 from the longitudinal axis of the LCP 602. In some cases, the docking member 638 may further include a tether retention structure 644 extending from or recessed within the head portion 640. The tether retention structure 644 may define an opening 646 configured to receive a tether or other anchoring mechanism therethrough. While the retention structure 644 is shown as having a generally "U-shaped" configuration, the retention structure 644 may take any shape that provides an enclosed perimeter surrounding the opening 646 such that a tether may be securably and releasably passed (e.g. looped) through the opening 646. In some cases, the retention structure 646 may extend though the head portion 640, along the neck portion 642, and to or into the proximal end 628 of the housing 626. The docking member 638 may be configured to facilitate delivery of the LCP 602 to the intracardiac site and/or retrieval of the LCP 602 from the intracardiac site. While this describes one example docking member 638, it is contemplated that the docking member 638, when provided, can have any suitable configuration.

It is contemplated that the LCP 602 may include one or more pressure sensors 648 coupled to or formed within the housing 626 such that the pressure sensor(s) is exposed to the environment outside the housing 626 to measure blood pressure within the heart. For example, if the LCP 626 is placed in the left ventricle, the pressure sensor(s) 648 may measure the pressure within the left ventricle. If the LCP 602 is placed in another portion of the heart (such as one of the atria or the right ventricle), the pressure sensor(s) may measure the pressure within that portion of the heart. The pressure sensor(s) 648 may include a MEMS device, such as a MEMS device with a pressure diaphragm and piezoresistors on the diaphragm, a piezoelectric sensor, a capacitor-Micro-machined Ultrasonic Transducer (cMUT), a condenser, a micro-monometer, or any other suitable sensor adapted for measuring cardiac pressure. The pressures sensor(s) 648 may be part of mechanical sensing circuitry. It is contemplated that the pressure measurements obtained from the pressures sensor(s) 648 may be used to generate a pressure curve over cardiac cycles. The pressure readings may be taken in combination with impedance measurements (e.g. the impedance between electrodes 632 and 634) to generate a pressure-impedance loop for one or more cardiac cycles as will be described in more detail below. The impedance may be a surrogate for chamber volume, and thus the pressure-impedance loop may be representative for a pressure-volume loop for the heart.

In some embodiments, the LCP 602 may be configured to measure impedance between the electrodes 632, 634. More generally, the impedance may be measured between other electrode pairs, such as the additional electrodes 546A-546B described above with respect to FIG. 5B. In some cases, the impedance may be measured between two spaced LCP's, such as two LCP's implanted within the same chamber (e.g. LV) of the heart, or two LCP's implanted in different chambers of the heart H (e.g. RV and LV). The processing circuitry of the LCP 602 and/or external support devices may derive a measure of cardiac volume from intracardiac impedance measurements made between the electrodes 632, 634 (or other electrodes). Primarily due to the difference in the resistivity of blood and the resistivity of the cardiac tissue of the heart, the impedance measurement may vary during a cardiac cycle as the volume of blood (and thus the volume of the chamber) surrounding the LCP changes. In some cases, the measure of cardiac volume may be a relative measure, rather than an actual measure. In some cases, the intracardiac impedance may be correlated to an actual measure of cardiac volume via a calibration process, sometimes performed during implantation of the LCP(s). During the calibration process, the actual cardiac volume may be determined using fluoroscopy or the like, and the measured impedance may be correlated to the actual cardiac volume.

In some cases, the LCP 602 may be provided with energy delivery circuitry operatively coupled to the first electrode 632 and the second electrode 634 for causing a current to flow between the first electrode 632 and the second electrode 634 in order to determine the impedance between the two electrodes 632, 634 (or other electrode pair). It is contemplated that the energy delivery circuitry may also be configured to deliver pacing pulses via the first and/or second electrodes 632, 634. The LCP 602 may further include detection circuitry operatively coupled to the first electrode 632 and the second electrode 634 for detecting an electrical signal received between the first electrode 632 and the second electrode 634. In some instances, the detection circuitry may be configured to detect cardiac signals received between the first electrode 632 and the second electrode 634.

When the energy delivery circuitry delivers a current between the first electrode 632 and the second electrode 634, the detection circuitry may measure a resulting voltage between the first electrode 632 and the second electrode 634 (or between a third and fourth electrode separate from the first electrode 632 and the second electrode 634, not shown) to determine the impedance. When the energy delivery circuitry delivers a voltage between the first electrode 632 and the second electrode 634, the detection circuitry may measure a resulting current between the first electrode 632 and the second electrode 634 (or between a third and fourth electrode separate from the first electrode 632 and the second electrode 634) to determine the impedance.

Figure 6:
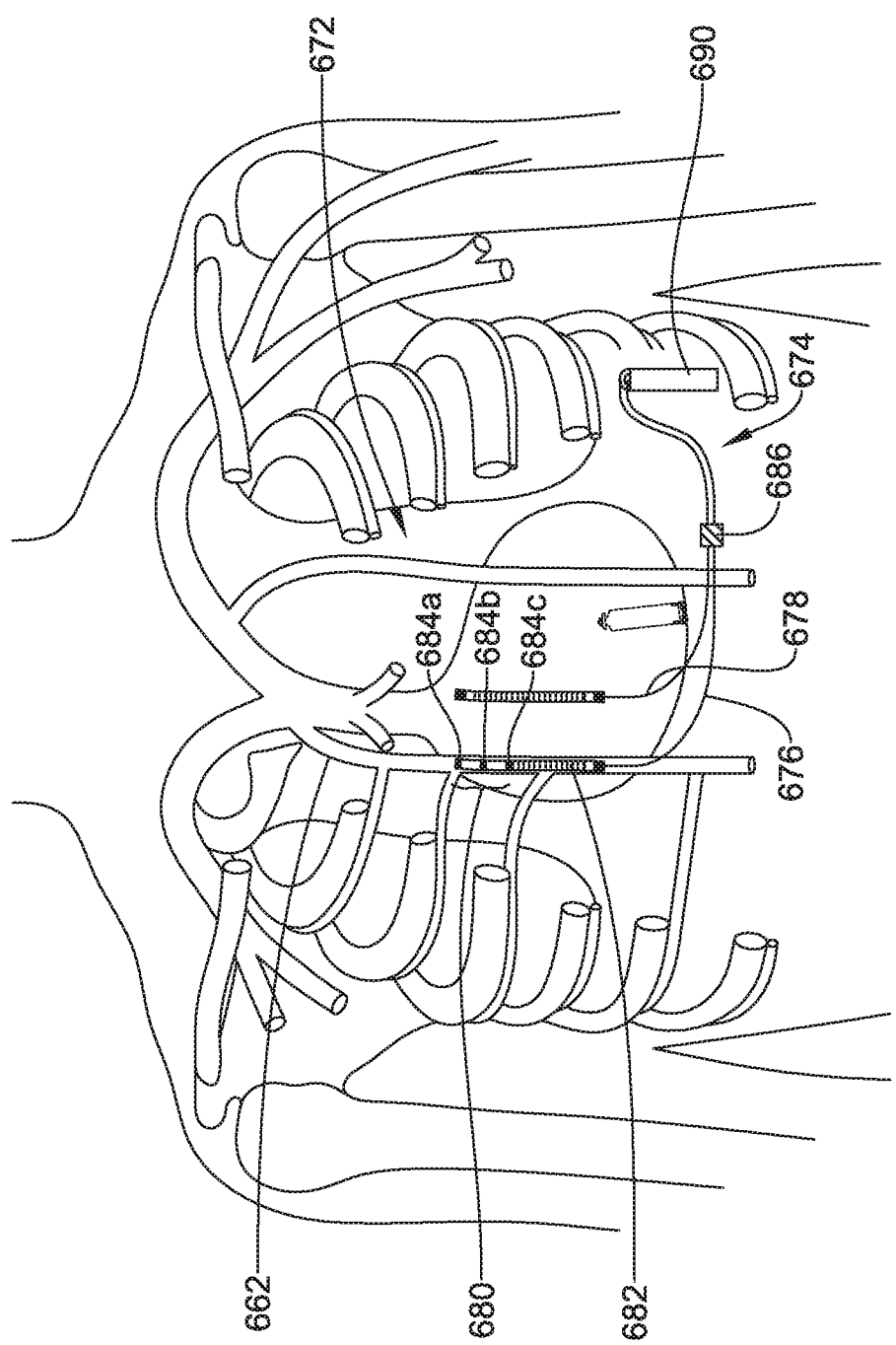
FIG. 6 illustrates thoracic anatomy with an implantable system for detecting an atrial event.

FIG. 6 illustrates portions of the thoracic anatomy including location of the left ITV 660 and the right ITV 662. The ribcage is shown at 668 and an outline of the heart is shown at 664. An implantable system 672 is also shown having a first medical device (MD) 674 (e.g., an implantable defibrillator) with a lead 676 located in the right ITV 662 and a lead 678 located next to a sternum of the patient. In certain embodiments, the lead 676 may include a distal sensing bipole 680 and a defibrillation electrode coil 682, as shown emplaced in the right ITV 662. As shown, the distal sensing bipole 680 may include electrodes 684A-684C spaced from one another and spaced distally from the defibrillation coil. Moreover, the lead 678 may include a defibrillation electrode coil 688, as shown emplaced in the chest cavity of the patient, such as just interior of the sternum but outside the heart 664. According to various embodiments, the distal portion of the leads 676, 678 may include a fixation apparatus or shape for the flexible lead, such as a 2 or 3 dimensional curve, tines, an expandable member, hooks, a side-extending engagement structure, etc.

Access to the ITVs 660, 662 may be achieved at any location, such as superior or inferior positions. FIG. 6 shows implantation from an inferior position in the right ITV 662. In this example, the right ITV 662 has been accessed by introduction through the superior epigastric vein from a location inferior to the rib margin 670. The first medical device 674 has been placed including the leads 676, 678 and a canister 690, with the canister 690 placed at approximately the left axilla. The canister 690 may be placed as desired, for example at the anterior axillary line, the midaxillary line, or in the posterior axillary line.

The musculophrenic vein may be accessed using similar methods as for the superior epigastric vein such as by ultrasound-guided Seldinger technique. Due to its adjacency to a bony structure (the inferior costal margin), the musculophrenic vein may be useful as its access may be simpler than that of the superior epigastric vein, as the position can be readily ascertained. Further details on use of the musculophrenic vein for ITV access can be found in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference.

In the illustration, a suture sleeve is shown at 686 and is used to fixate the leads 676, 678, for example, to the subcutaneous fascia. For placement of the lead 676, the right ITV 662 may be accessed and a tunnel established between the left axilla and the access location such as along a portion of the inframammary crease. The lead 676 may, in this case, be relatively stiff to assist in keeping it emplaced in the patient as shown, if desired. The tunnel may also be used for placement of the lead 678 in the chest of the patient.

In the example of FIG. 6, a left axillary canister location is shown; a right sided, pectoral or subclavicular left or right position may be used instead, in combination with the right ITV 662 placement, the left ITV 660, and/or intercostal vein placement.

The ITV's 660, 662 may be accessed via their corresponding superior epigastric or musculophrenic veins using standard access techniques known in the art for implanting traditional transvenous pacemakers and defibrillators. For example, access may be achieved using ultrasound guided needle insertion. The access method may resemble the Seldinger technique. Other venipuncture or cutdown techniques may be used instead.

The Seldinger technique may include creating a puncture at the desired access location, with a hollow needle or trocar, for example under ultrasound guidance, introducing a guidewire through the needle and into the desired blood vessel, removing the needle, keeping the guidewire in place, and then inserting an introducer sheath, which may have a valve at its proximal end, over the guidewire. The introducer sheath may be advanced to a location to place its distal tip near a desired location. Contrast injection may be useful to visualize the musculophrenic vein, superior epigastric vein, ITV and/or intercostal vein structures. A guide catheter and guidewire may then be introduced through the introducer sheath. The guidewire may be the same as used in gaining initial access (if one is used to gain access), or may be a different guidewire. In another example, a cut-down technique may be used to access the desired vein by incision through the skin. The incision may be made laterally from the location of the desired vein. Next, possibly after visual confirmation the desired vessel is accessed, incision into the selected vein can be made, followed by insertion of the lead. Once access to a selected superior epigastric or musculophrenic vein is achieved, the vessel can be traversed in a superior direction to place the lead 676 with the electrodes 684A-684C and the defibrillation coil 682 at the desired level by entering the corresponding ITV.

Various approaches for use of the ITV are shown in U.S. Provisional Patent Application No. 62/423,638, filed Nov. 17, 2016, the entire contents of which are herein incorporated by reference.

The leads 676, 678 may be tunneled from the parasternal access location across and down to the canister 690, which may be implanted at the left axilla as illustrated. For ease of illustration the canister 690 is shown at about the anterior axillary line, level with the cardiac apex and/or inframammary crease. In other examples the canister 690 may be more lateral and/or posterior, such as at the mid-axillary line or posterior axillary line, or may even be more dorsal with placement dorsally between the anterior surface of the serratus and the posterior surface of the latissimus dorsi. A right sided axillary, pectoral or subclavicular left or right position may be used instead, in combination with right, left ITV, or intercostal vein placement.

In some examples, a flexible lead may be introduced with the support of a guide catheter during advancement. The guide catheter may receive the lead through a guide catheter lumen that serves to retain a fixation apparatus or shape for the flexible lead, such as a 2-dimensional or 3-dimensional curvature, tines, an expandable member, or hooks or a side-extending engagement structure. A stylet may be placed through the lead, or a portion thereof, to retain a straight shape during implantation; upon removal of the stylet, a curvature may then be released for securing the lead in place.

In another alternative, the guide catheter and guidewire may be omitted by providing a lead with a flexible or steerable structure, and/or a lead configured for implantation using a steerable stylet. For example, a lead may be configured to be implanted using a steerable stylet in a lumen thereof, with the initial placement into the left ITV 660 (or right ITV 662 or an intercostal vein, if desired) at the distal end of the introducer sheath, possibly using contrast visualization, if desired. Once initial access is achieved, simply pushing the stylet should be sufficient to implant the lead to a desired level in the ITV. The stylet may have a secondary function of preventing an anchoring structure of the lead from assuming an anchoring shape or releasing an anchoring tine, hook, expandable member, stent or other device. In other examples, a guidewire and/or sheath may not be needed. Due to the limited angulation required for accessing the ITV from a parasternal incision, the lead may be inserted directly into the ITV, reducing the time and complexity of the procedure.

The leads 676, 678 shown in FIG. 6 include the defibrillating coil electrodes 682 and 688 and three ring electrodes 684A-684C disposed longitudinally along the coil. The ring electrodes 684A-684C may serve as sensing and/or defibrillating electrodes. The coil electrodes 682 and canister may serve as therapy delivery electrodes.

FIG. 6 also depicts the system 672 in which the first MD 674 may perform sensing for an atrial event, detects the atrial event and communicates to a second MD 692 of the system 672, such as an LCP. The second MD 692 may receive the communication and then deliver pacing therapy to the heart 664. In some examples, the second medical device 692 may be located in the right ventricle (RV). In other examples, the second MD 692 may be located in another chamber of the heart 664, such as the left ventricle (LV). The communication may take the form of a command to pace, or may instead simply provide information or directions such as that an atrial event has been sensed and the proper therapy to provide.

The atrial event may be an electrical signal detection, such as a P-wave, or likely P-wave, has been detected. See, for example, US PG Patent Application Pub. No. 20170368360, titled CARDIAC THERAPY SYSTEM USING SUBCUTANEOUSLY SENSED P-WAVES FOR RESYNCHRONIZATION PACING MANAGEMENT, the disclosure of which is incorporated herein by reference, for examples using a second device to detect an atrial electrical signal for use in CRT pacing. The atrial event may be a mechanical event instead, indicating atrial contraction. See, for example, US PG Patent Application Pub. No. 20180008829, titled METHOD AND SYSTEM FOR DETERMINING AN ATRIAL CONTRACTION TIMING FIDUCIAL IN A LEADLESS CARDIAC PACEMAKER SYSTEM, the disclosure of which is incorporated herein by reference, for examples of the LCP or a second device detecting an atrial mechanical signal for use in CRT pacing. For example, the S4 heart sound, which indicates atrial contraction may be detected and relied upon. In another example the A-wave, a pressure wave indicating atrial contraction, may be detected and relied upon.

The electrical P-wave or other atrial event sensing may be difficult from a subcutaneous-only location in some environments such as a noisy environment, or may be difficult in certain patients due to abnormal conduction, placement of sensing electrodes, etc. P-wave or other atrial event sensing may also be difficult if a patient has an atrial arrhythmia that prevents such sensing, for example, if a patient starts to experience atrial fibrillation. Patient movement and/or the patient's environment may affect the ability to sense a mechanical signal as well. This has led to interest in further alternative implantation locations, such as the ITV, for implanting atrial sensing devices to capture P-waves, analyze the P-waves, determine proper pacing therapy directions, and communicate the pacing therapy directions to other devices to potentially optimize the pacing therapy delivered.

According to various embodiments, the first MD 674 may sense electrical signals (e.g., atrial cardiac signals) due to the depolarization of the heart 664 via the distal sensing bipole 680 located in the right ITV 662. In some examples, the first MD 674 may use the electrode pair 684A and 684B to create the sensing bipole 680. In other examples, the first MD 674 may use the electrode pair 684A and 684C to create the sensing bipole 680. In other examples, the first MD 674 may use the electrode pair 684B and 684C to create the sensing bipole 680. In yet further examples, the first MD 674 may use two or all three electrode pair combinations to create a dual or tri-sensing bipole 680. The implant position in the ITV may be selected to place the bipole 680 more or less level with the atria of the patient. Pre-implant and during implant imaging may be used to plan and/or verify such positioning. Pre-implant surface (transcutaneous) sensing may be performed to identify a desirable position as well.

In certain embodiments, the depolarization signal may be transmitted to operational circuitry (not shown in FIG. 6) disposed within the housing of the first MD 674 via the lead. In some cases, the operational circuitry may include sensing circuitry to sense or locate the P-waves in the depolarization signal and then analyze or measure at least one characteristic of P-waves. Exemplary characteristics of P-waves that may be measured by the first MD 674 may include amplitudes, variability of widths, dispersion of widths, etc. In cases where the first MD 674 analyzes the amplitude of the P-waves, in some embodiments, the first MD 674 may sample the P-wave amplitudes over a period of time and calculate an average value and/or a range of acceptable amplitude values. The sensing circuitry may then receive additional P-waves and compare their amplitude with the average value and/or range of acceptable amplitude values. The sensing circuitry may then detect abnormalities based on the comparison and determine an appropriate pacing therapy that should be administered to the heart 664. In various embodiments, the operational circuitry of the first MD 674 may include communication circuitry configured to send the pacing therapy instructions to the second MD 692 and the second MD 692 may then deliver the appropriate pacing therapy to the heart 664, such as anti-tachycardia pacing (ATP) therapy, cardiac resynchronization therapy (CRT), bradycardia therapy, Vdd pacing and/or the like. In some cases, the appropriate pacing therapy may include defibrillation therapy, such as cardioversion/defibrillation therapy. In these cases, the first MD 674 may deliver the appropriate therapy autonomously or in combination with the second MD 692 using the defibrillation coil 682 and/or 688.

In cases where the first MD 674 analyzes the width of the P-waves, in some embodiments, as was the case with the determination of average P-wave amplitudes, the first MD 674 may sample the P-wave widths over a period of time and calculate an average value and/or a range of acceptable width values. The sensing circuitry may then receive additional P-waves and compare their width with the average value and/or range of acceptable width values. The sensing circuitry may then detect abnormalities based on the comparison and determine an appropriate pacing therapy that should be administered to the heart 664. Accordingly, the first MD 674 may communicate with the second MD 692 to deliver the appropriate pacing therapy and/or deliver the appropriate therapy autonomously or in combination with the second MD 692.

As stated herein, in various embodiments, the first MD 674 may use both or several electrode pair combinations of 684A, 684B and 684C to create a dual or tri-sensing bipole 680. In these cases, the lead 676 may use bipole pair combinations to track the atrial depolarization via muliple vectors. For example, using the serial sequence of bipoles 684A and 684B, 684A and 684C, and 684B and 684C, the first MD 674 may obtain timing information to enhance P-wave detection. In some cases, the local atrial activation activity on the bipoles may march in certain temporal patterns. As a result, P-wave detection may be confirmed not just based on amplitude or width, but on seeing the temporal profile of activity across the multiple electrode pairs. Accordingly, the propagation information along with other characteristics of the P-waves (e.g., amplitude and width) within the depolarization signal may help locate and confirm detection of subsequent P-waves.

In certain embodiments, such as embodiments utilizing multiple bipole pairs, the P-wave detection may benefit from a horizontal circumferential arrangement where at least a portion of the lead 676 is also located in an intercostal vein or a brachiocephalic vein. In this configuration, the accuracy of the timing information may be increased by analyzing the temporal separation of activity received by the bipole pairs.

In addition to monitoring the propagation of the P-wave, the system may receive other portions of the cyclic cardiac signal for analysis. For example, timing from the P-wave to the Q or R-wave, or begin or end of the QRS complex, may be assessed. Such timing can inform determinations relating to CRT and may help tailor CRT therapy, for example. P-wave detection and R-wave detection may also be used to determine whether atrial and ventricular events are occurring at a 1:1 ratio, as mismatch may be indicative of a range of arrhythmias.

Figure 7:
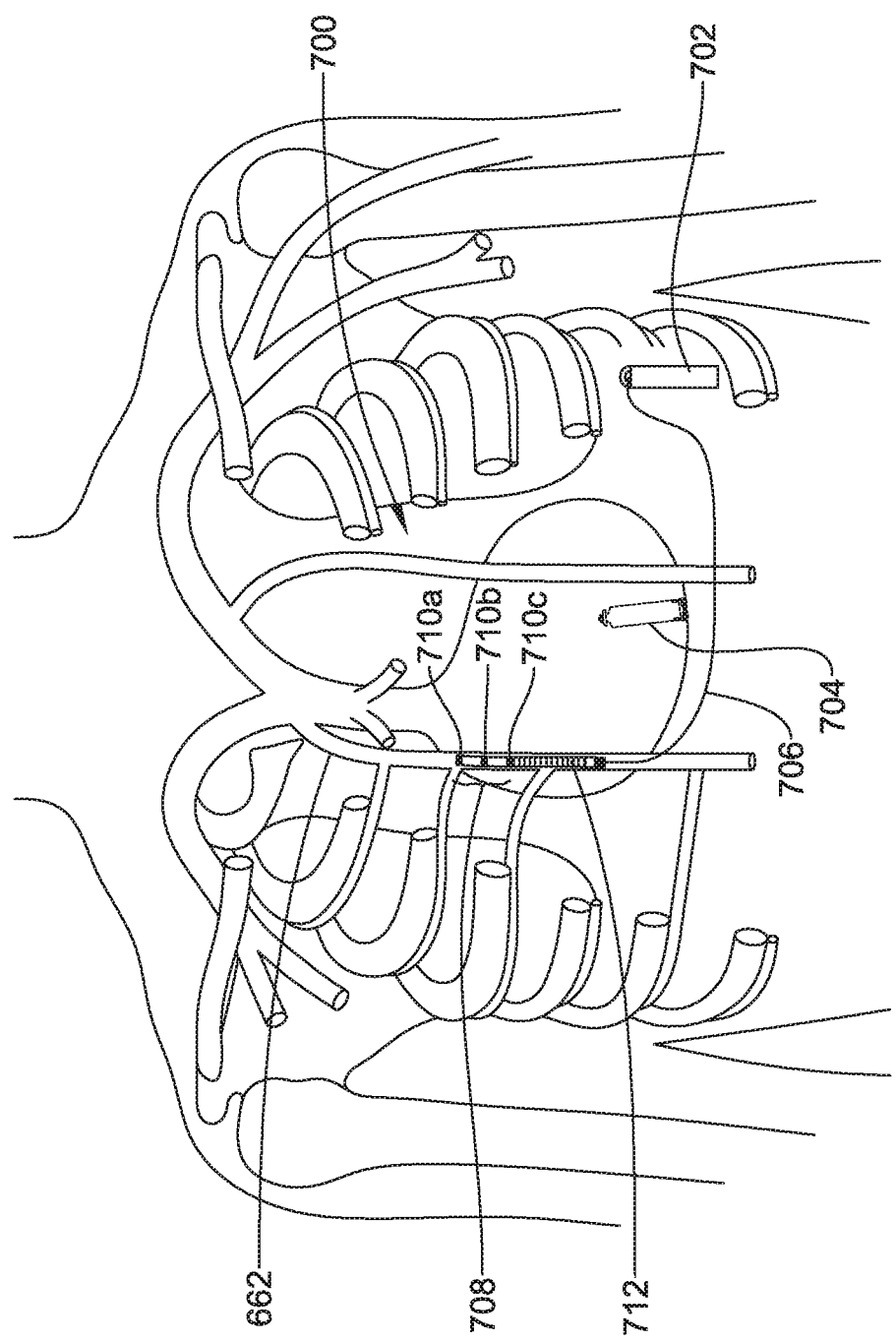
FIG. 7 illustrates the thoracic anatomy with another implantable system for detecting an atrial event.

FIG. 7 shows another system 700 in which a first MD 702 may perform sensing for an atrial event, detects the atrial event and communicates to a second MD 704. The configuration and operation of the system 700 may be similar to the configuration and operation of the system 672, described in regard to FIG. 6. However, in this embodiment, the first MD 702 only has one lead 706 in the right ITV 662. As shown, the lead 706 includes distal sensing bipole 708 electrodes 710A-710C spaced from one another and distally spaced from a defibrillation coil 712. The first MD 702 may determine pacing and/or defibrillation therapy needs of the patient, and can use the defibrillation coil 712 and the active canister of the first MD 702 for delivery of defibrillation therapy.

Figure 8:
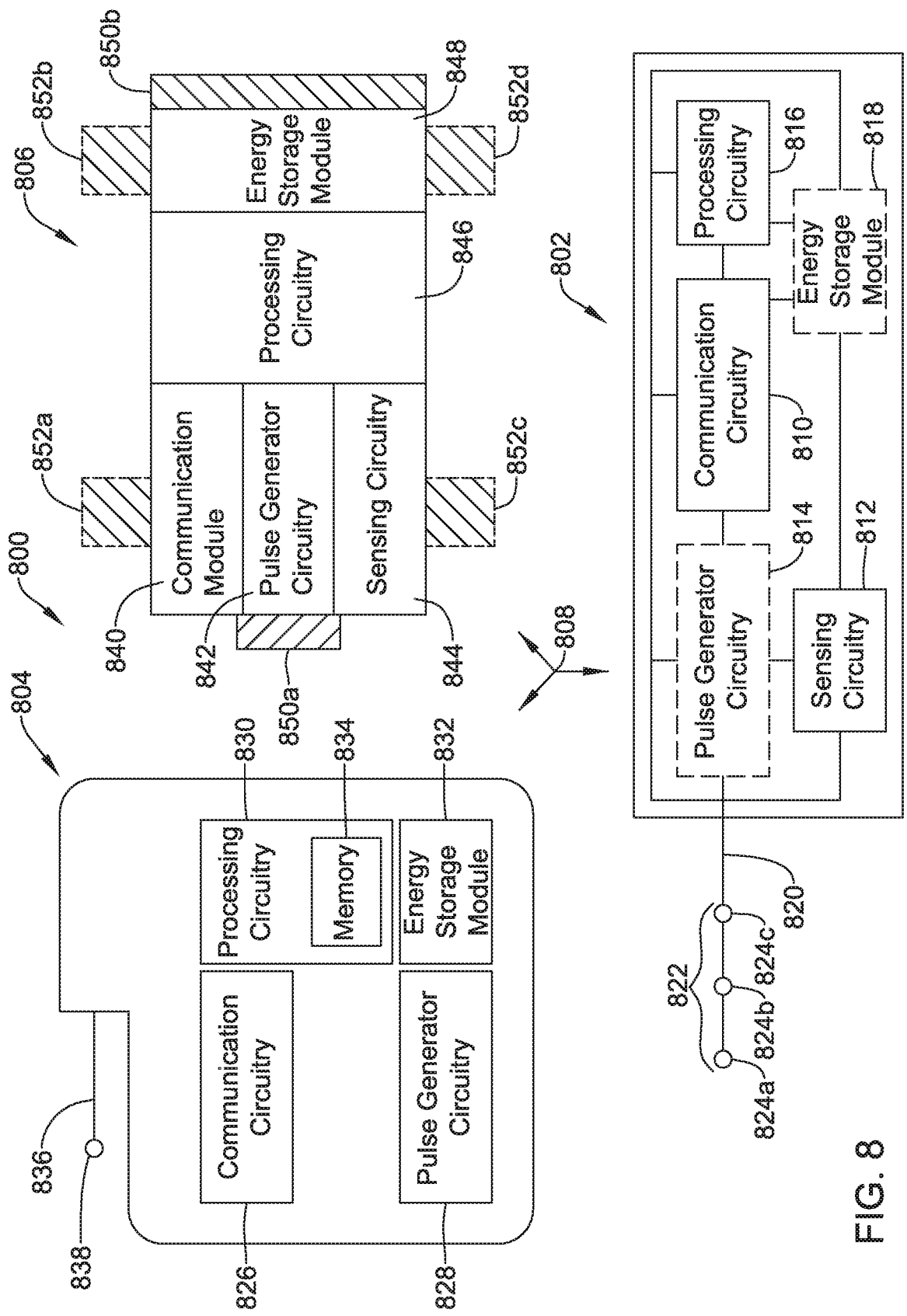
FIG. 8 illustrates another implantable system.

FIG. 8 depicts another example of an implantable system 800 that may be implanted into a patient and may operate to deliver appropriate therapy to the heart. In various embodiments, the system 800 may include a first MD 802, a second MD 804, and a third MD 806. In addition, the system 800 may also include a communication pathway 808 similar to the communication pathway 550 from FIG. 5B.

In the example shown, the MD 804 may include communication circuitry 826, pulse generator circuitry 828, and processing circuitry 830. Each of these circuitries may be similar to the circuitries 506, 510, and 512 of the IMD 500. Additionally, memory 834 and energy storage module 832 may be similar to the memory 516 and the energy storage module 514 of the IMD 500. Furthermore, the IMD 804 may be configured with a lead 836 having an electrode 838, similar to the lead 524 and electrode 526D of the IMD 500.

In various embodiments, the third MD 806 may include communication circuitry 840, pulse generator circuitry 842, sensing circuitry 844, and processing circuitry 846. Each of these circuitries may be similar to the circuitries 534, 536, 538, and 540 of the MD 532, from FIG. 5B. Additionally, an energy storage module 848 may be similar to the energy storage module 542 of the MD 532. Furthermore, the third MD 806 may include electrodes 850A, 850B and 852A-852D similar to the electrodes 544A, 544B and 546A-546D of the MD 532.

In the example shown, the first MD 802 may include communication circuitry 810, optional pulse generator circuitry 814, sensing circuitry 812, and processing circuitry 816. Each of these circuitries may be similar to the circuitries 506, 508, 510, and 512 of the IMD 500. Additionally, the first MD 802 may also include an optional energy storage module 818 that may be similar to the energy storage module 514 of the IMD 500. Furthermore, the first MD 802 may be configured with a lead 820. The lead 820 may have three electrodes 824A-824C capable of forming sensing bipoles similar to electrodes 526A-526C of the IMD 500. The lead 820 may be adapted for placement subcutaneously and/or in the ITV, as desired.

Figure 9:
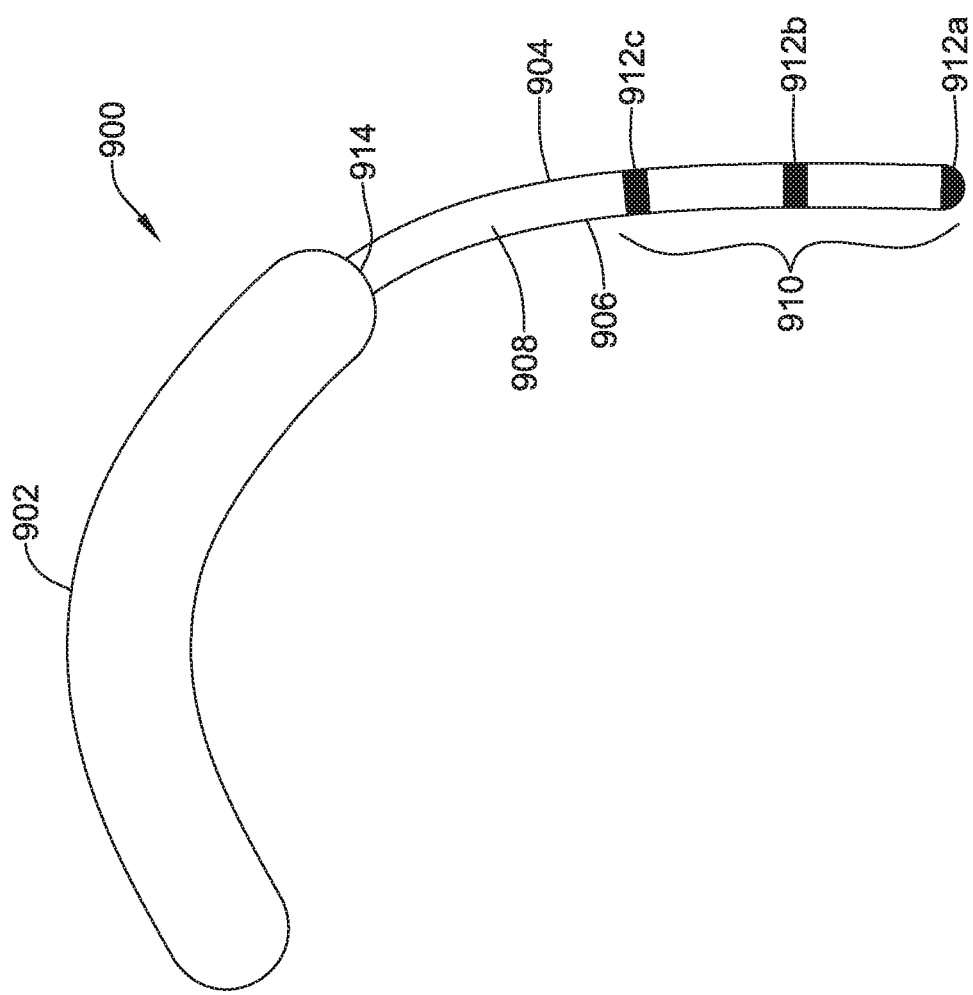
FIG. 9 illustrates another implantable medical device (IMD)

FIG. 9 depicts an illustrative IPG 900. In various embodiments, the IPG may be an example of the first MD 802, from FIG. 8. In such examples, the IPG 900 may include a housing 902 having circuitry that includes sensing circuitry and communication circuitry (e.g., the sensing circuitry 812 and the communication circuitry 810, from FIG. 8) disposed within. Additionally, lead 904, similar to lead 820, may be connected to the circuitry and extend away from the housing 902.

In certain embodiments, the lead 820 may include a bipolar sensing electrode pair 910 at a distal end 906 adapted for atrial sensing. In some cases, the bipolar sensing pair 910 may include tip electrode 912A and electrode 912B spaced proximally away from the electrode 912A. In other cases, the bipolar sensing pair 910 may include the tip electrode 912A and electrode 912C spaced proximally away from the electrode 912A. In other cases, the bipolar sensing pair 910 may include the electrode 912B and the electrode 912C. In yet further embodiments, the lead 904 may have two or three bipolar sensing electrode pairs 910 that include two or three combinations of the electrodes 912A-912C.

In various embodiments, the lead 904 may have a proximal end 908 that includes a proximal connector 914 configured to attach the lead 904 to the housing 902 and couple the electrodes 912A-912C to the internal circuitry (i.e., the sensing circuitry, the communication circuitry, the pulse generator circuitry, etc.) of the IPG 900. In certain embodiments, the lead 904 may also include a hollow interior extending from the proximal end 908 to the distal end 906. The hollow interior may allow for the introduction of a stylet (not shown) during implant, which may allow the lead 904 to be guided through a point of venous insertion to an implant site (e.g., an ITV and/or an intercostal vein).

Figure 10:
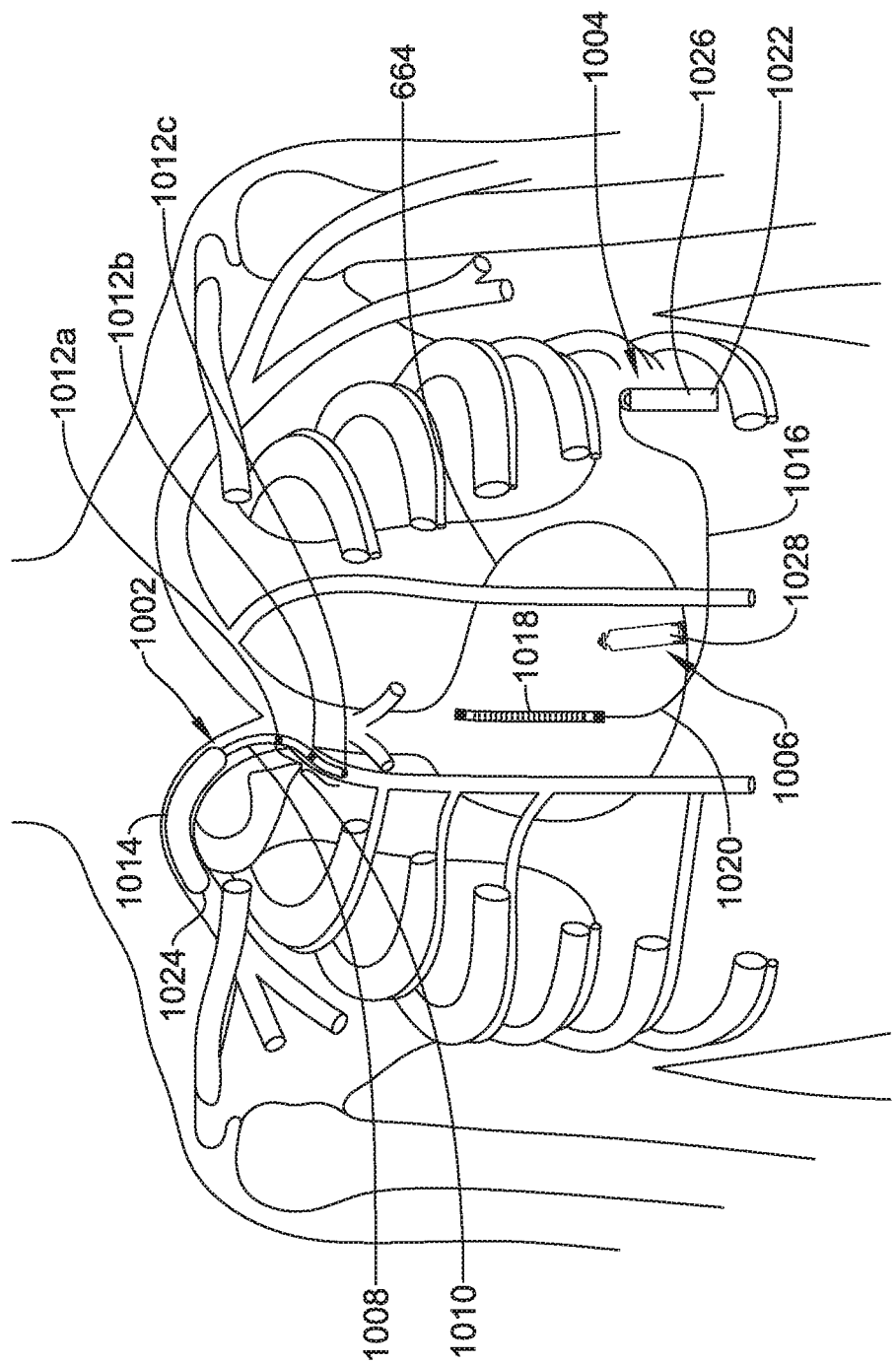
FIG. 10 illustrates the thoracic anatomy with another implantable system for detecting an atrial event.

FIG. 10 illustrates portions of the thoracic anatomy including location of the left ITV 660 and the right ITV 662 and an implantable system having a first medical device MD 1002, a second MD 1004, and a third MD 1006. The ITV's 660, 662, intercostal veins, and/or brachiocephalic vein may be accessed using standard access techniques similar to the accessing techniques discussed in regard to FIG. 6.

In certain embodiments, the first MD 1002 may include a lead 1008 in the right ITV 662. In certain embodiments, the lead 1008 may include a distal sensing bipole 1010. As shown, the distal sensing bipole 1010 may include electrodes 1012A-1012C spaced from one another. According to various embodiments, the distal portion of the lead 1008 may include a fixation apparatus or shape for the lead 1008, such as a 2 or 3 dimensional curve, tines, an expandable member, hooks, a side-extending engagement structure, etc. Parasternal access to the ITVs 660, 662 may be achieved at any location, such as superior or inferior positions.

FIG. 10 shows implantation from a superior position in the right ITV 662. In this example, the right ITV 662 has been accessed by introduction through a brachiocephalic vein 1014. The first MD 1002 may have a housing 1024 adapted and sized for placement near the clavicle in a subcutaneous or submuscular position. Alternatively, the first MD 1002 may itself be advanced into one of the blood vessels in the region including, as shown, in the brachiocephalic vein itself. It is envisioned however that a subcutaneous, right sided position may be used in many cases. FIG. 10 is not intended to be specific to one or the other positions (subcutaneous, submuscular, or within-vein).

The first MD 1002 may be configured to only sense atrial cardiac activity in some examples, and may omit pulse generator circuitry/capability. In other examples, the first MD may be adapted to deliver therapy as by including pacing output circuitry or higher energy defibrillation output circuitry as described above in various examples.

In various embodiments, the configuration and operation of the second MD 1004 may be similar to the first MD 690 from FIG. 6. However, in this embodiment, the second MD 1004 only has one lead 1016 located next to a sternum of the patient. As shown, the lead 1016 includes a defibrillation coil electrode 1018 on a distal end 1020. The defibrillating coil electrode 1018 may serve as defibrillating electrodes. The coil electrode 1018 and canister 1022 may serve as therapy delivery electrodes. According to various embodiments, the distal end 1020 of the lead 1016 may include a fixation apparatus or shape for the lead 1016, such as a 2 or 3 dimensional curve, tines, an expandable member, hooks, a side-extending engagement structure, etc. The lead 1016 may be implanted subcutaneously over the sternum, mediastinally under the sternum, or in the left ITV, if desired.

In certain embodiments, the configuration and operation of the third MD 1006 may be similar to the second MD 692 from FIG. 6. In some examples, the third MD 1006 may be located in the right ventricle (RV). In other examples, the third MD 1006 may be located in another chamber of the heart 664, such as the left ventricle (LV).

According to various embodiments, a housing 1024 of the first MD 1002 may contain sensing circuitry to observe electrical signals (e.g., atrial cardiac signals) due to the depolarization of the heart 664 sensed using the distal sensing bipole 1010 located in the right ITV 662. In some examples, the first MD 1010 may use the electrode pair 1012A and 1012B to create the sensing bipole 1010. In other examples, the first MD 1002 may use the electrode pair 1012A and 1012C to create the sensing bipole 1010. In other examples, the first MD 1002 may use the electrode pair 1012B and 1012C to create the sensing bipole 1010. In yet further examples, the first MD 1002 may use two or all three electrode pair combinations to create a dual or tri-sensing bipole 1010. Exemplary characteristics of P-waves that may be measured or analyzed by the first MD 1002 may include amplitudes, variability of widths, dispersion of widths, etc. In certain embodiments, the housing 1024 of the first MD 1002 may also contain communication circuitry configured to send the atrial cardiac signal to the second MD 1004, or to send a communication indicating a result of analysis of the atrial cardiac signal performed by the first MD 1002 to the second MD 1004.

In certain embodiments, a housing 1026 of the second MD 1004 may also contain communication circuitry configured to receive communications from the first MD 1002. If the first IMD 1002 communicates the atrial cardiac signal, the second IMD 1004 may perform analysis thereof and make decisions related to arrhythmia detection and/or pacing therapy control. If the first IMD 1002 communicates results from its analysis of the atrial cardiac signal, the second IMD may use such results to inform or control arrhythmia detection and/or pacing therapy decisions. In various embodiments, the communication circuitry of the second MD 1004 may be further configured to send the pacing therapy instructions to the third MD 1006.

In various embodiments, the third MD 1006 may have a housing 1028 that contains communication circuitry configured to receive the pacing therapy instructions from the second MD 1004. The housing 1028 may also contain therapy circuitry that is configured to deliver the pacing therapy to the heart 664, based on the pacing therapy instructions. For example, the third MD 1006 may provide anti-tachycardia pacing (ATP) therapy, cardiac resynchronization therapy (CRT), bradycardia therapy, Vdd pacing and/or the like. In some cases, the appropriate pacing therapy may include defibrillation therapy, such as cardioversion/defibrillation therapy. In these cases, the second MD 1004 may deliver the appropriate therapy autonomously or in combination with the third MD 1006 using the defibrillation coil 1018.

In certain embodiments, the second MD 1004 and associated lead are omitted such that the implantable system includes the third MD 1006 and the first MD 1002 and excludes the second MD 1004. Such a configuration may be useful for a patient needing only pacing and lacking an ICD indication. In an example, the first MD 1002 captures cardiac signals and identifies an atrial event such as a P-wave and communicates to the third MD 1006 to command pacing or otherwise confirm or modify a pace therapy delivered by the third MD 1006 in accordance with the embodiments herein. In another example, the first MD 1002 captures cardiac signal (and other data, as desired) for diagnostic purposes, such as for identification of atrial arrhythmias or heart failure status.

In various embodiments, a mechanical sensor such as an accelerometer, for example, may be disposed in any of the devices of discussed herein. Furthermore, in some cases, multiple devices may have a mechanical sensor including the first MD 1002, the second MD 1004, and the third MD 1004 of FIG. 10. Such mechanical sensors may include an accelerometer to identify patient posture and/or activity level, a pressure sensor to detect changes in blood pressure, and/or a detector for sound such as a piezoelectric element adapted to capture heart sounds or sounds associated with respiration or patient activity. Other sensors, such as optical sensors to detect blood analytes and/or blood flow may be included as well.

As stated herein, in various embodiments, the first MD 1002 may use both or several electrode pair combinations of 1012A, 1012B and 1012C to create a dual or tri-sensing bipole 1010. In these cases, the lead 1008 may use bipole pair combinations to track the atrial depolarization via multiple vectors. For example, using the serial sequence of bipoles 1012A and 1012B, 1012A and 1012C, and 1012B and 1012C, the first MD 1002 may obtain timing information to enhance P-wave detection. In some cases, the local atrial activation activity on the bipoles may march in certain temporal patterns. As a result, P-wave detection may be confirmed not just based on amplitude or width, but on seeing the temporal profile of activity across the multiple electrode pairs. Accordingly, the propagation information along with other characteristics of the P-waves (e.g., amplitude and width) within the atrial cardiac signal may help locate and confirm detection of subsequent P-waves.

In certain embodiments, such as embodiments utilizing multiple bipole pairs, the P-wave detection may benefit from a horizontal circumferential arrangement where at least a portion of the lead 1008 is also located in an intercostal vein or a brachiocephalic vein. In this configuration, the accuracy of the timing information may be increased by adjusting the temporal separation of activity received by the bipole pairs.

Figure 11:
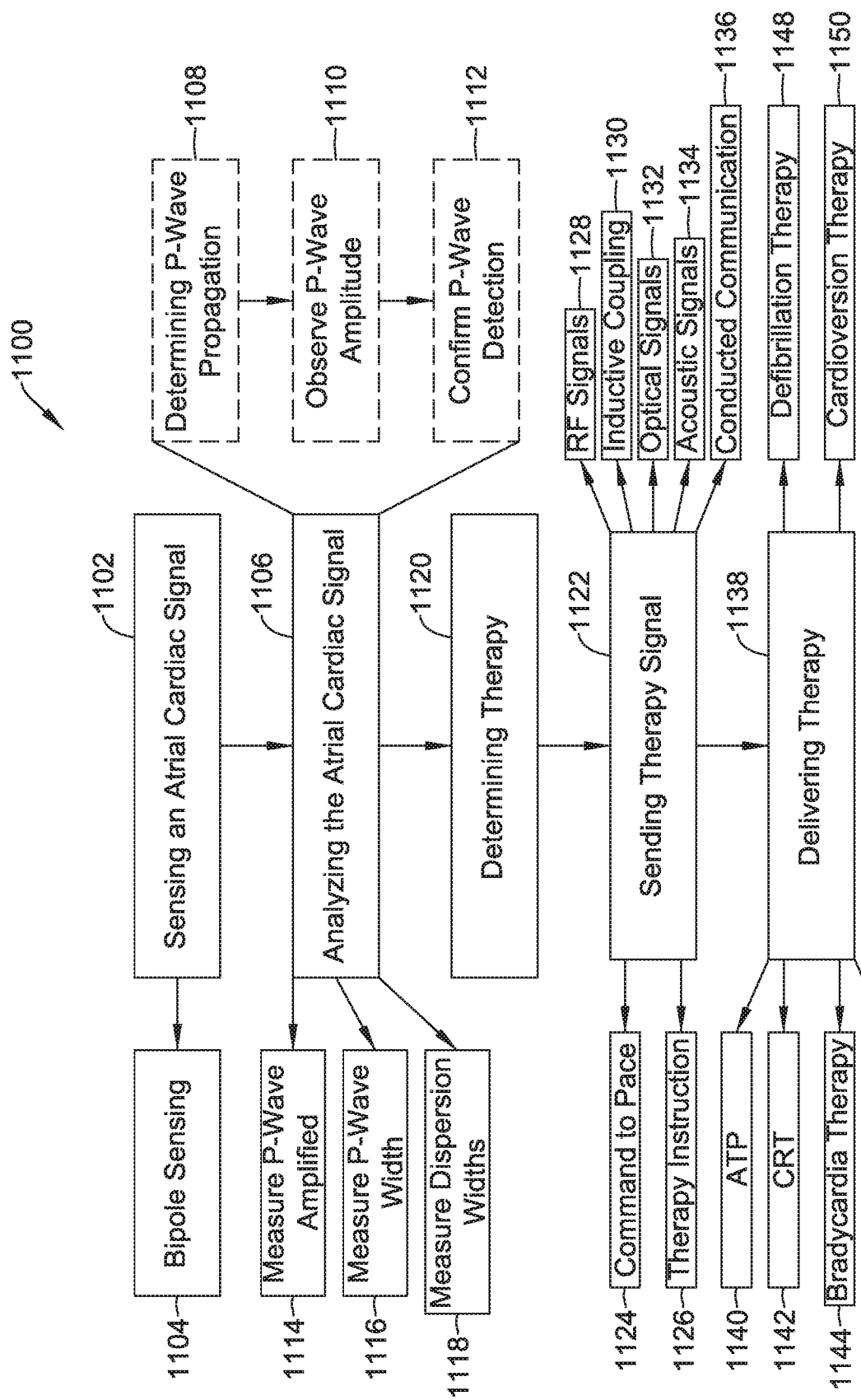
FIG. 11 is a block flow diagram for an illustrative method.

FIG. 11 is a block flow diagram for an illustrative method of treating a patient. As shown at 1100, the method comprises sensing an atrial cardiac signal 1102, analyzing the atrial cardiac signal 1106, determining a therapy 1120, sending a therapy signal 1122, and delivering the therapy 1138.

For example, in some examples, a system may be used having a first implantable medical device (IMD) and a second IMD. In some examples, the first MD may be an implantable defibrillator having a lead emplaced in an ITV of a patient or a lead placed subcutaneously outside the ribs of the patient, or having a lead placed in the mediastinum beneath the sternum. The lead may include at least two electrode structures configured as a bipole for atrial sensing. In some examples sensing the atrial cardiac signal 1102 may include using the first IMD to perform bipole sensing 1104 of the atrial cardiac signal using the two electrode structures.

In an example, analyzing the atrial cardiac signal 1106 may include an optional p-wave signal detection subroutine. In some examples, the first IMD may include multiple sensing bipoles. In these cases, the first IMD may use various electrode pair combinations to track the atrial depolarization via multiple vectors. For example, using the serial sequence of bipoles, the first IMD may obtain timing information to enhance P-wave detection in the atrial cardiac signal. In some examples, the local atrial activation activity on the bipoles may march in certain temporal patterns. As a result, P-wave detection may be confirmed not just based on amplitude or width, but on seeing the temporal profile of activity across the multiple electrode pairs. Accordingly, the P-wave propagation may be determined 1108 from the temporal profile. Furthermore, in some examples, the P-wave amplitude may be observed 1110 from the atrial cardiac signal. The first IMD may then us the P-wave propagation along with the P-wave amplitude characteristics within the atrial cardiac signal to help locate and confirm detection of subsequent P-waves 1112. Divergence from expected P-wave propagation may indicate supraventricular arrhythmia such as atrial fibrillation (AF) and observation of such divergence may be used as a marker for AF in some examples.

Alternatively or additionally, analyzing the atrial cardiac signal 1106 may include measuring at least one characteristic of the P-waves. In some examples, the amplitude of the P-waves may be measured 1114. For example, the first IMD may sample the P-wave amplitudes over a period of time and calculate an average value and/or a range of acceptable amplitude values. The first IMD may then receive additional P-waves and compare their amplitude with the average value and/or range of acceptable amplitude values. Additionally or alternatively, in some examples, the width of the P-waves may be measured 1116. For example, as was the case with the amplitude measurement, the first IMD may sample the P-wave widths over a period of time and calculate an average value and/or a range of acceptable width values. The first IMD may then receive additional P-waves and compare their width with the average value and/or range of acceptable width values. Additionally or alternatively, in some examples, the dispersion of the P-wave widths may be measured 1116.

In an example, determining a therapy 1120 may be based on the comparison between the amplitude of the current P-wave received and the average value and/or range of acceptable amplitude values. Additionally or alternatively, in some examples, determining the therapy 1120 may be based on the comparison between the width of the current P-wave received and the average value and/or range of acceptable width values. Additionally or alternatively, in some examples, determining the therapy 1120 may be based on the comparison between the dispersion of the width of the current P-wave received and the average value and/or range of acceptable dispersion values.

In an example, the first IMD may be communicatively coupled to a second IMD. The second IMD may be placed in or adjacent to the heart of the patient. In some examples, the second IMD may be a leadless cardiac pacemaker (LCP). In some examples, sending the therapy signal 1122 may include the first IMD sending the therapy signal to the second IMD. In some examples, the therapy signal may take the form of a command to pace 1124. In some examples, the therapy signal may provide information or directions such as that a P-wave has been analyzed and the proper therapy to provide 1126. Furthermore, in some examples, in some examples, the first IMD may send the signal via radiofrequency (RF) signals 1128, inductive coupling 1130, optical signals 1132, acoustic signals 1134, conducted communication signals 1136, and/or any other signals suitable for communication.

In an example, delivering the therapy 1138 may include the second IMD delivering anti-tachycardia pacing (ATP) therapy 1140, cardiac resynchronization therapy (CRT) 1142, bradycardia therapy 1144, or Vdd pacing 1146. Alternatively or additionally, in some examples, delivering the therapy 1138 may include the first IMD delivering defibrillation therapy 1148 and/or cardioversion therapy 1150.

Figure 12:
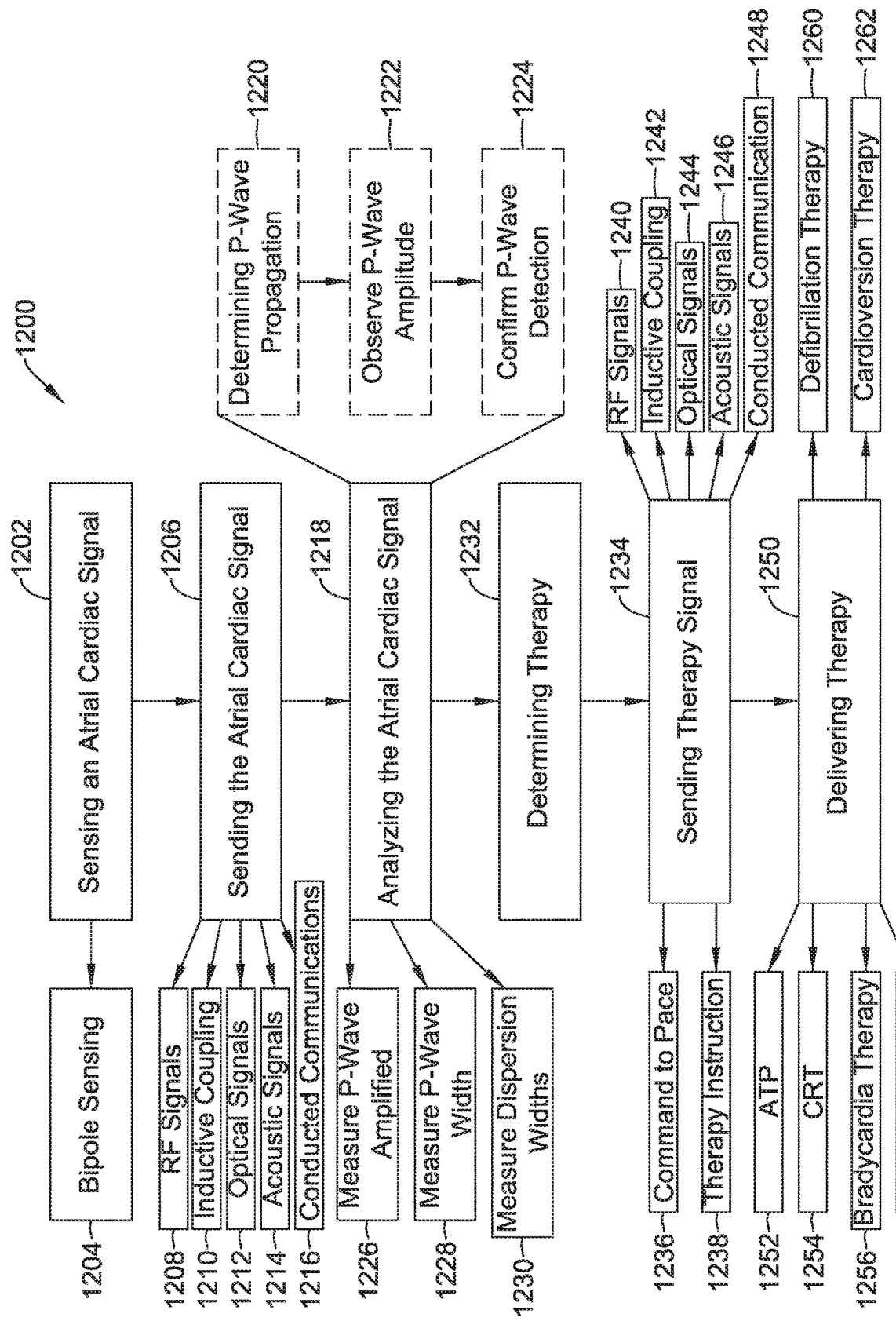
FIG. 12 is a block flow diagram for another illustrative method.

FIG. 12 is a block flow diagram for another illustrative method of treating a patient. As shown at 1200, the method comprises sensing an atrial cardiac signal 1202, sending the atrial cardiac signal 1206, analyzing the atrial cardiac signal 1218, determining a therapy 1232, sending a therapy signal 1234, and delivering the therapy 1250.

For example, a system may be used having a first IMD, a second IMD, and a third IMD. In some examples, the first IMD include a lead emplaced in an ITV of a patient. The lead may include at least two electrode structures configured for bipole sensing. In some examples sensing the atrial cardiac signal 1202 may include using the first IMD to perform bipole sensing 1204 of the atrial cardiac signal using the two electrode structures. The first IMD may or may not include therapy delivery circuitry.

In an example, the first IMD may be communicatively coupled to the second IMD. In some examples, the second IMD may be an implantable defibrillator, such as an S-ICD, having a lead emplaced in the chest cavity of the patient, such as just interior of the sternum but outside the heart. In some examples, the lead may include a defibrillation coil electrode, configured to deliver defibrillation therapy. In some examples, sending the atrial cardiac signal 1206 may include the first IMD sending the atrial cardiac signal to the second IMD. In other examples, the first IMD may instead send a result of its analysis of the atrial cardiac signal at block 1206, rather than sending a digitized form of the signal itself. In some examples, the first IMD may send the signal via radiofrequency (RF) signals 1208, inductive coupling 1210, optical signals 1212, acoustic signals 1214, conducted communication signals 1216, and/or any other signals suitable for communication.

In an example, analyzing the atrial cardiac signal 1218 may be done similar to the examples discussed in regard to step 1106, of flow diagram 1100. In an example, determining a therapy may be done similar to the examples discussed in regard to step 1120, of flow diagram 1100.

In an example, the third IMD may be a leadless cardiac pacemaker (LCP) and sending a therapy signal 1234 may be done similar to the examples discussed in read to step 1122, of flow diagram 1100. In an example, delivering the therapy 1250 may be done similar to the examples discussed in regard to step 1138, of flow diagram 1100.

Some embodiments of the present invention may take the form of an implantation tool set configured for use in implanting a cardiac device, such as a lead, into an ITV. Some such embodiments may include an introducer sheath. Some such embodiments may include a guide catheter. Some such embodiments may include a guidewire. Some such embodiments may further include a tool set for performing a Seldinger technique to access a blood vessel percutaneously.

Some embodiments of the present invention take the form of an implantable cardiac stimulus device comprising a lead and an implantable canister for coupling to the lead, the implantable canister housing operational circuitry configured to deliver output therapy in the form of at least one of bradycardia pacing, anti-tachycardia pacing, cardiac resynchronization therapy, or defibrillation, using a lead implanted in an ITV and a canister implanted in a patient.

As used herein, a coil electrode may be a helically wound element, filament, or strand. The filament forming the coil may have a generally round or a generally flat (e.g. rectangular) cross-sectional shape, as desired. However, other cross-sectional shapes may be used. The coil electrode may have a closed pitch, or in other words, adjacent windings may contact one another. Alternatively, the coil electrode may have an open pitch such that adjacent windings are spaced a distance from one another. The pitch may be uniform or varied along a length of the coil electrode. A varied pitch may be gradual tapered changes in pitch or abrupt or step-wise changes in pitch.

A coil electrode may have a length L that is generally larger than a width W. Round, oval or flattened coil electrodes may be used. Coil electrodes may have a length in the range of one to ten centimeters. In an example, a coil having a six or eight centimeter length may be used. In another example, a lead may have two four centimeter coils. Coils and leads may be in the range of four to ten French, or larger or smaller, in outer profile. Rather than a coil electrode, a cylindrical electrode may be used having a continuous surface.

Coils and leads may be coated. For example, a thin permeable membrane may be positioned over a shock coil or other electrode and/or other portions of the lead to inhibit or to promote tissue ingrowth. Coatings, such as, but not limited to expanded polytetrafluoroethylene (ePTFE) may also be applied to the coil and/or lead to facilitate extraction and/or to reduce tissue ingrowth. In some embodiments, one or more of the electrodes, whether coils, rings, or segmented electrodes, include a high capacitive coating such as, but not limited to iridium oxide (IrOx), titanium nitride (TiN), or other "fractal" coatings which may be used, for example, to improve electrical performance. Steroidal and antimicrobial coatings may be provided as well.

The various components of the devices/systems disclosed herein may include a metal, metal alloy, polymer, a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers for use in the leads discussed above may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like.

In at least some embodiments, portions or all of the accessory devices and their related components may be doped with, made of, or otherwise include a radiopaque material. Radiopaque materials are understood to be materials capable of producing a relatively bright image on a fluoroscopy screen or another imaging technique during a medical procedure. This relatively bright image aids the user of the accessory devices and their related components in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the accessory devices and their related components to achieve the same result.

Any guidewire, introducer sheath, and/or guide catheter design suitable for medical interventions may be used for accessing the venous structures discussed herein.

The implantable systems shown above may include an implantable pulse generator (IPG) adapted for use in a cardiac therapy system. The IPG may include a hermetically sealed canister that houses the operational circuitry of the system. The operational circuitry may include various elements such as a battery, and one or more of low-power and high-power circuitry. Low-power circuitry may be used for sensing cardiac signals including filtering, amplifying and digitizing sensed data. Low-power circuitry may also be used for certain cardiac therapy outputs such as pacing output, as well as an annunciator, such as a beeper or buzzer, telemetry circuitry for RF, conducted or inductive communication (or, alternatively, infrared, sonic and/or cellular) for use with a non-implanted programmer or communicator. The operational circuitry may also comprise memory and logic circuitry that will typically couple with one another via a control module which may include a controller or processor. High power circuitry such as high power capacitors, a charger, and an output circuit such as an H-bridge having high power switches may also be provided for delivering, for example, defibrillation therapy. Other circuitry and actuators may be included such as an accelerometer or thermistor to detected changes in patient position or temperature for various purposes, output actuators for delivering a therapeutic substance such as a drug, insulin or insulin replacement, for example.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like and may include computer readable instructions for performing methods. Further, in an example, code can be tangibly stored on volatile, non-transitory, or non-volatile tangible computer-readable media, such as during execution or at other times.

Examples of tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of treating a patient comprising:
   sensing an atrial cardiac signal using a first electrode located in an internal thoracic vein (ITV) of the patient and a second electrode, the first electrode and the second electrode operatively coupled to a first medical device;
   analyzing a P-wave from the atrial cardiac signal using the first medical device;
   determining a therapy using the first medical device based on the analyzed P-wave; and
   sending a therapy instruction to a second medical device communicatively coupled to the first medical device.

2. The method of claim 1, further comprising delivering the therapy to the patient using the second medical device based on the therapy instruction.

3. The method of claim 1 wherein the first medical device is further operatively coupled to a third electrode and the first and second electrodes form a first sensing bipole adapted for atrial sensing, and the third electrode forms, with one of the first or second electrodes, a second sensing bipole adapted for atrial sensing, the method further comprising:
   determining propagation of the P-wave using the first and second bipoles;
   observing an amplitude of the P-wave using the first medical device; and
   confirming detection of the P-wave based on the propagation and the amplitude using the first medical device.

4. The method of claim 1 wherein the first medical device is placed in the patient on the right side of the chest at a subcutaneous or submuscular positon near the clavicle, and the first and second electrodes are disposed on a lead attached to the first medical device and extending into the right brachiocephalic vein and thence into the right ITV, to a desired position relative to the atria.

5. The method of claim 1 wherein the first medical device is placed in the patient on the left side of the chest at an axillary position, and the first and second electrodes are disposed on a lead attached to the first medical device extending medially therefrom to a parasternal location adjacent the sternum and then through an intercostal between two ribs and into the ITV.

6. The method of claim 1, wherein the first medical device is an implantable cardioverter defibrillator.

7. The method of claim 1, wherein the second medical device is a leadless cardiac pacemaker (LCP) located in a heart of the patient.

8. The method of claim 1, wherein the therapy comprises cardiac resynchronization therapy.

9. The method of claim 1, wherein the therapy comprises Vdd pacing.

10. The method of claim 1 wherein the therapy instruction is a pace command.

11. The method of claim 10 wherein the method further comprises the second medical device issuing a pacing pulse.

12. The method of claim 1 wherein the first medical device comprises a housing containing operational circuitry for sensing atrial signals, and omits a pulse generator, the housing adapted for placement in a blood vessel, wherein the method is performed with the first medical device housing located in a brachiocephalic vein of the patient.

* * * * *